United States Patent
Jin et al.

(10) Patent No.: US 9,346,781 B2
(45) Date of Patent: May 24, 2016

(54) THERAPEUTIC COMPOUNDS

(71) Applicant: UNIVERSITY OF IOWA RESEARCH FOUNDATION, Iowa City, IA (US)

(72) Inventors: Zhendong Jin, Iowa City, IA (US); Lei Chen, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 14/417,043

(22) PCT Filed: Jul. 25, 2013

(86) PCT No.: PCT/US2013/052081
§ 371 (c)(1),
(2) Date: Jan. 23, 2015

(87) PCT Pub. No.: WO2014/018765
PCT Pub. Date: Jan. 30, 2014

(65) Prior Publication Data
US 2015/0210664 A1 Jul. 30, 2015

Related U.S. Application Data

(60) Provisional application No. 61/675,665, filed on Jul. 25, 2012, provisional application No. 61/720,785, filed on Oct. 31, 2012.

(51) Int. Cl.
| | | |
|---|---|---|
| C07D 313/00 | (2006.01) |
| C07D 307/88 | (2006.01) |
| A61K 9/00 | (2006.01) |
| A61K 9/12 | (2006.01) |
| A61K 9/20 | (2006.01) |
| A61K 9/48 | (2006.01) |
| C07F 7/18 | (2006.01) |
| C07F 7/22 | (2006.01) |
| C07C 233/18 | (2006.01) |

(52) U.S. Cl.
CPC ............ *C07D 313/00* (2013.01); *A61K 9/0019* (2013.01); *A61K 9/12* (2013.01); *A61K 9/2018* (2013.01); *A61K 9/2054* (2013.01); *A61K 9/4858* (2013.01); *C07C 233/18* (2013.01); *C07D 307/88* (2013.01); *C07F 7/1856* (2013.01); *C07F 7/1892* (2013.01); *C07F 7/2212* (2013.01); *C07C 2101/14* (2013.01); *C07C 2101/16* (2013.01)

(58) Field of Classification Search
CPC .................................................... C07D 313/00
USPC ....................................................... 514/450
See application file for complete search history.

(56) References Cited

PUBLICATIONS

King, Med. Chem., Principle and Practice (1994), pp. 206-208.*
Bhatnagar et al., "Marine antitumor drugs: status, shortfalls and strategies", Mar. Drugs 8, 2702-2720 (2010).
Chen et al., "Design, Synthesis, and Biological Evaluation of Truncated Superstolide A", Angrewandte Chemical Int. Ed. vol. 52, 3446-3449 (2013).
D'Auria et al., "Superstolide A: a potent cytotoxic macrolide of a new type from the New Caledonian deep water marine sponge Neosiphonia superstes", J. Am. Chem. Soc. 116 (15), 6658-6663 (1994).
D'Auria et al., "A novel cytotoxic macrolide, superstolide B, related to superstolide A, from the New Caledonian marine sponge Neosiphonia superstes", J. Nat. Prod. 57, 1595-1597 (1994).
Mei, "Syntheses of natural products OSW-1, superstolide A and their derivatives", The University of Iowa, Doctoral Thesis, 1-218 (2009).
Patent Cooperation Treaty, International Searching Authority, PCT Search Report and Written Opinion for PCT/US2013/52081, 14 pages, Jan. 8, 2014.
Pubchem, Ethly Acrylate Compound Summary, CID 8821, retrieved on Dec. 10, 2013 from URL: http://pubchem.ncbi.nlm.nih.gov/summary/summary.cgi?cid=8821&loc=ec_rcs>; p. 1, (2005).
Qi et al., "The medicinal potential of promising marine macrolides with anticancer activity", ChemMedChem 6, 399-409 (2011).
Shah et al., "Studies towards synthesis of truncated Supertolide A", poster presentation, the 22nd Biocatalysis and Bioprocessing Conference, Oct. 21-22, 2013, the University of Iowa, Iowa City, IA.
Shah et al., "Syntheis and biological evaluation of truncated Supertolide A", poster presentation, the 22nd Biocatalysis and Bioprocessing Conference, Oct. 21-22, 2013, the University of Iowa, Iowa City, IA.
Zampella et al., "Studies towards the synthesis of superstolide A. Synthesis and stereochemical assignment of the C(21)-C(26) fragment of superstolide A", Tetrahedron: Asymmetry 12, 1543-1545 (2001).
Tortosa, et al., "Total Synthesis of (+)-Superstolide A", Journal of Organic Chemistry, vol. 73 (24), 9657-9667 (2008).
Yu, et al., "Synthetic Studies of Antitumor Natural Products Superstolides A and B. Construction of C20-C26 Fragment of Superstolide A", Organic Letters, vol. 3 (10), 1447-1450 (2001).

\* cited by examiner

*Primary Examiner* — Taofiq A Solola
(74) *Attorney, Agent, or Firm* — Viksnins Harris & Padys PLLP

(57) ABSTRACT

The invention provides compounds useful as anti-cancer agents.

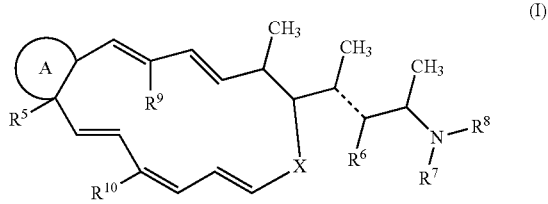

19 Claims, 1 Drawing Sheet

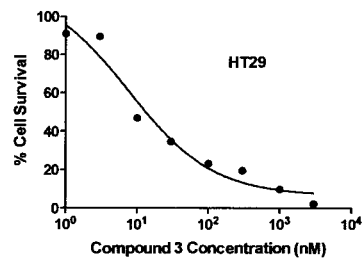
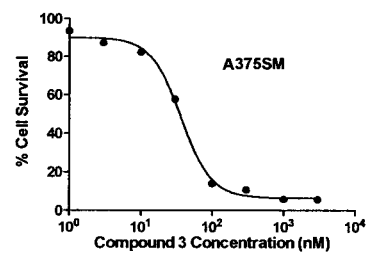
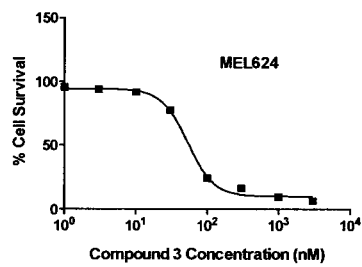
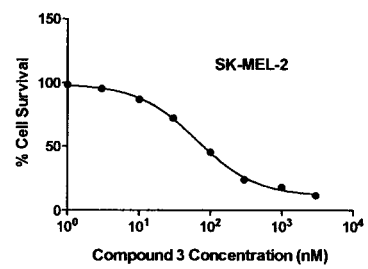
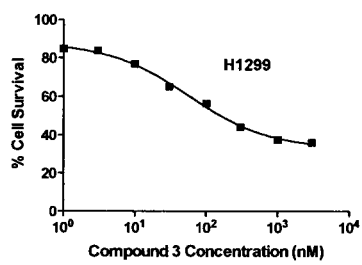
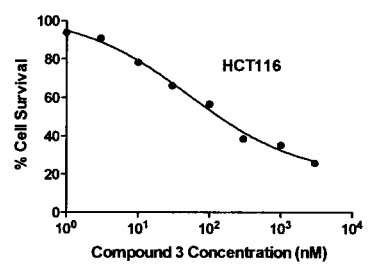
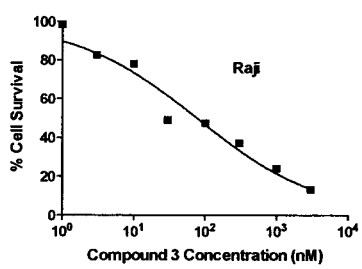
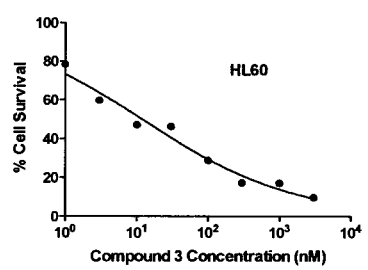
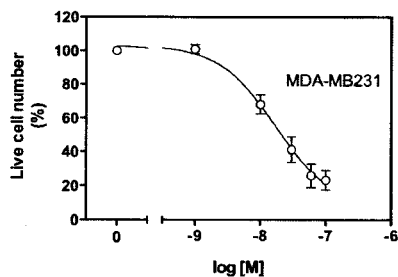

THERAPEUTIC COMPOUNDS

PRIORITY OF INVENTION

This application claims priority to U.S. Provisional Application No. 61/675,665, filed 25 Jul. 2012, and to U.S. Provisional Application No. 61/720,785, filed 31 Oct. 2012. The entire content of each of these provisional applications is incorporated herein by reference.

STATEMENT REGARDING FEDERALLY FUNDED RESEARCH

This invention was made with government support under Grant Number R01 CA109208 awarded by the National Institutes of Health. The Government has certain rights in the invention.

BACKGROUND OF THE INVENTION

Marine natural products are of considerable interest because of their structural novelty, functional diversity and potent biological activity. In particular, marine macrolides are well known for their fascinating molecular structure and potent anticancer activity (see Qi, Y.; Ma, S. *Chem Med Chem* 2011, 6, 399; and Bhatnagar, I., et al., *Mar. Drugs* 2010, 8, 2702). Superstolides A (1) and B (2), two marine macrolides, were isolated in minute amounts from the deep-water marine sponge *Neosiphonia superstes* (see D'Auria, M. V., et al., *J Am. Chem. Soc.* 1994, 116, 6658; and D'Auria, M. V et al., *J. Nat. Prod.* 1994, 57, 1595). Their absolute structures were determined by extensive spectroscopic methods. The structural novelty of these two molecules is characterized by a unique 16-membered macrolactone attached to a functionalized cis-decalin.

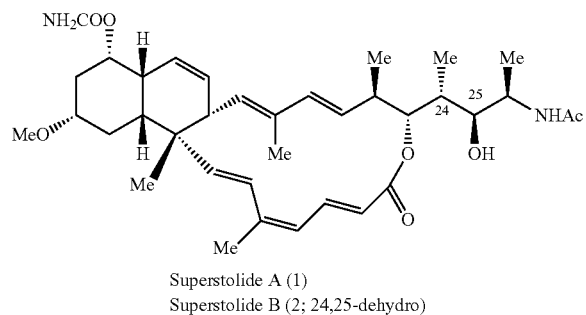

Superstolide A (1)
Superstolide B (2; 24,25-dehydro)

Both superstolides A and B exhibit potent antiproliferative effect against several tumor cell lines with $IC_{50}$ values ranging from 4.8 to 64 nM. Their structures are novel and unprecedented, suggesting that they might have a unique cellular target(s) and a novel mechanism of action. Unfortunately, the isolation yields for both superstolides A and B are only 0.003% and 0.0003%, respectively. In addition, the marine sponge *Neosiphonia superstes* live at 500-515 meters deep in the ocean off New Caledonia, which makes the collection of the sponge very difficult and dangerous. Furthermore, collecting a large amount of marine sponge has the potential to cause significant damage to the marine habitat. Due to the scarcity of these compounds there has not been enough material for further biological investigation, a common problem in the study of biologically active marine natural products. The potent anticancer activities coupled with their challenging molecular structures have attracted a great deal of attention from the synthetic organic chemistry community.

Currently there is a need for novel compounds that can be prepared on a commercial useful scale and that retain the useful pharmacologic properties of superstolide A and B. Such compounds would be useful not only as therapeutic agents for the treatment of cancer, but also as pharmacologic tools for further studying the mechanism of action of superstolide A and B.

SUMMARY OF THE INVENTION

Accordingly the invention provides compound of formula I:

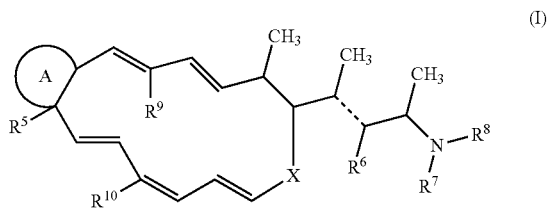

(I)

wherein:

Ring A is a 5-7 membered monocyclic or an 8-12 membered bicyclic, saturated, partially unsaturated, or aromatic, carbocyclic or heterocyclic ring system that is optionally substituted with one or more groups independently selected from hydroxy, halo, nitro, cyano, trifluoromethoxy, $(C_1-C_6)$alkyl, $(C_1-C_6)$alkoxy, $(C_1-C_6)$alkanoyl, $(C_1-C_6)$alkoxycarbonyl, or $(C_3-C_6)$cycloalkyl, wherein the $(C_3-C_6)$cycloalkyl and $(C_1-C_6)$alkyl are each optionally substituted with one or more OH, SH, halo, or $N(R_a)_2$;

$R^5$ is H, hydroxy, mercapto (—SH), halo, $N(R_a)_2$, or $(C_1-C_6)$alkyl, wherein the $(C_1-C_6)$alkyl is optionally substituted with one or more hydroxy, mercapto, halo, or $N(R_a)_2$; or $R^5$ is absent when it is not required to fill the valence requirements of the ring A atom to which it is attached;

either the bond represented by ---- is a double bond and $R^6$ is H; or the bond represented by ---- is a single bond and $R^6$ is H, hydroxy, or $N(R_b)_2$;

$R^7$ is H, $(C_3-C_6)$cycloalkyl, or $(C_1-C_6)$alkyl;

$R^8$ is C(=O)$R_c$, C(=O)O$R_c$, —S(=O)$R_c$, —S(=O)$_2R_c$, —C(=O)N$R_aR_e$;

$R^9$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;

$R^{10}$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;

X is —C(=O)—O—, —O—C(=O)—, —C(=O)—N$R_a$—, —N$R_a$C(=O)—, —O—C(=O)—N$R_a$—, —N$R_a$—C(=O)—O—, —O—C(=O)—O—, or —N$R_a$—C(=O)—N$R_a$—;

each $R_a$ is independently H or $(C_1-C_6)$alkyl;
each $R_b$ is independently H or $(C_1-C_6)$alkyl;
$R_c$ is H, $(C_3-C_6)$cycloalkyl, or $(C_1-C_6)$alkyl;
$R_d$ is H, $(C_3-C_6)$cycloalkyl, or $(C_1-C_6)$alkyl; and
$R_e$ is H, $(C_3-C_6)$cycloalkyl, or $(C_1-C_6)$alkyl;
or a salt thereof.

The invention also provides a pharmaceutical composition comprising a compound of formula I or a pharmaceutically acceptable salt thereof, and a pharmaceutically acceptable excipient.

The invention also provides a method for treating or preventing cancer in an animal (e.g. a mammal such as a human) comprising administering a compound of formula I or a pharmaceutically acceptable salt thereof to the animal.

The invention also provides a compound of formula I or a pharmaceutically acceptable salt thereof for use in medical therapy.

The invention also provides a compound of formula I or a pharmaceutically acceptable salt thereof for the prophylactic or therapeutic treatment of cancer.

The invention also provides the use of a compound of formula I or a pharmaceutically acceptable salt thereof to prepare a medicament for treating cancer in an animal (e.g. a mammal such as a human).

The invention also provides processes and intermediates disclosed herein that are useful for preparing a compound of formula I or a salt thereof.

BRIEF DESCRIPTION OF THE FIGURES

FIG. 1 Illustrates results generated when HT29, A375SM, MEL624, SK-MEL-2, H1299, HCT116, Raji, HL60 and MDA-MB231 cells were treated with log-scale serial diluted concentrations of truncated superstolide A (Compound 3) from 1 to 3000 nM for 72 hours and the effect of truncated superstolide A on cell death was measured by performing a MTT assay.

DETAILED DESCRIPTION

The following definitions are used, unless otherwise described: Alkyl denotes both straight and branched groups; but reference to an individual radical such as propyl embraces only the straight chain radical, a branched chain isomer such as isopropyl being specifically referred to.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

Specific values listed below for radicals, substituents, and ranges, are for illustration only; they do not exclude other defined values or other values within defined ranges for the radicals and substituents. Specifically, $(C_1-C_6)$alkyl can be methyl, ethyl, propyl, isopropyl, butyl, iso-butyl, sec-butyl, pentyl, 3-pentyl, or hexyl.

When ring A is a 5-7 membered monocyclic or 8-12 membered bicyclic carbocyclic group it includes monocyclic and bicyclic carbocycles that can be saturated, partially unsaturated, or aromatic. Examples of such groups include cyclopentane, cyclohexane, cycloheptane, cyclopentene, cyclohexene, cycloheptene, phenyl, naphthyl, tetrahydronaphthyl, bicyclo [4,4,0]decane, and the like. When $R^5$ is attached to an aromatic ring A or to an unsaturated carbon in ring A, $R^5$ is absent.

When ring A is a 5-7 membered monocyclic or an 8-12 membered bicyclic heterocyclic ring system the ring system includes one or more (e.g. 1, 2, 3, or 4) heteroatoms selected from O, S, and N, as well as one or more carbon atoms. The ring system can be saturated, partially unsaturated, or aromatic. The ring system can also optionally be substituted on one or more carbon, nitrogen, or sulfur with oxo. Examples of such ring systems include pyridine, pyrrole, piperidine, quinolone, isoquinoline, and the like. When $R^5$ is not required to fill the valence requirements of the ring A atom to which it is attached, $R^5$ will be absent.

In one embodiment of the invention the compound of formula (I) is a compound of formula Ia:

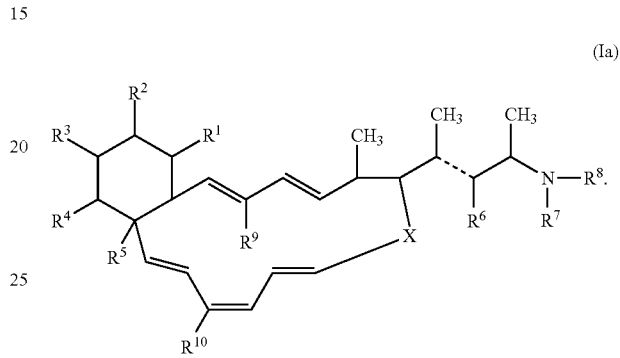

(Ia)

In one embodiment of the invention the compound of formula (I) is a compound of formula Ib:

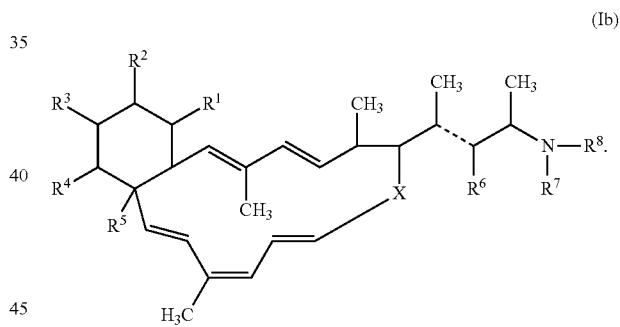

(Ib)

In one embodiment of the invention the compound of formula (I) is a compound of formula Ic:

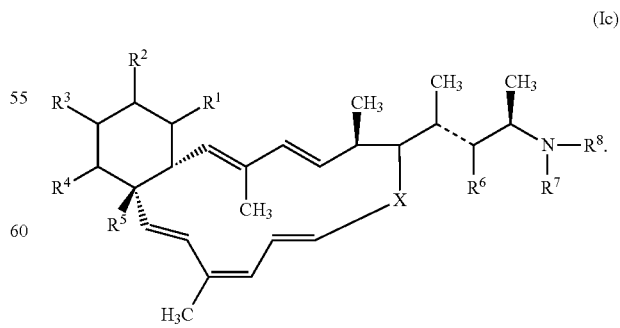

(Ic)

In one embodiment of the invention the compound of formula (I) is a compound of formula Id:

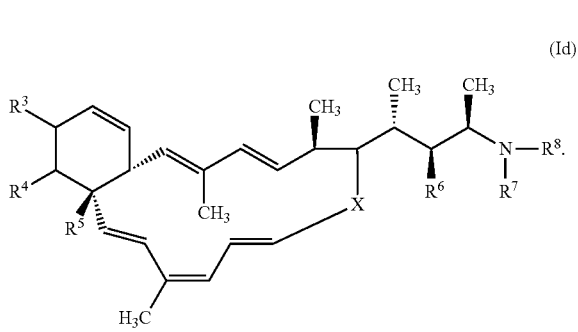

(Id)

In one embodiment of the invention the compound of formula (I) is a compound of formula Ie:

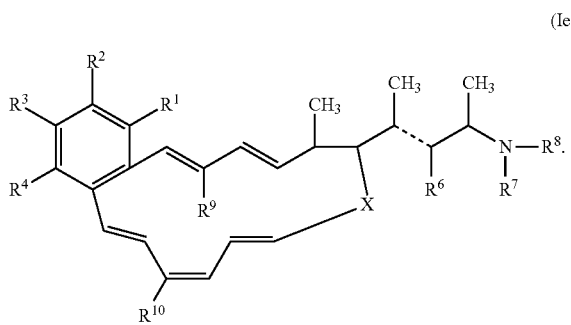

(Ie)

In one embodiment of the invention the compound of formula (I) is a compound of formula If:

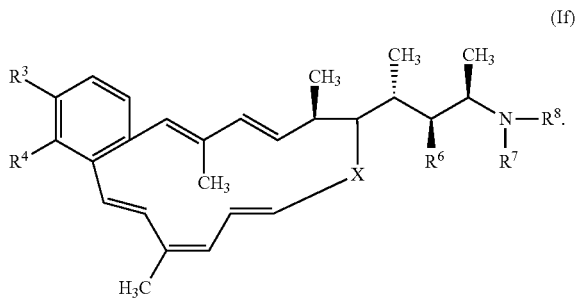

(If)

In one specific embodiment $R^1$ and $R^2$ are each H.

In one specific embodiment $R^1$ and $R^2$ taken together with the atoms to which they are attached form a double bond.

A specific value for $R^3$ is H.
A specific value for $R^4$ is H.
A specific value for $R^5$ is methyl.
A specific value for $R^6$ is H.
In one embodiment the bond represented by ---- is a single bond and $R^6$ is hydroxy.
A specific value for $R^7$ is H.
A specific value for $R^9$ is trifluoromethyl.
A specific value for $R^{10}$ is trifluoromethyl.
A specific value for $R^8$ is —C(=O)$R_c$.
A specific value for X is —C(=O)—O— or —O—C(=O)—.
A specific value for X is —C(=O)—NR$_a$— or —NR$_a$C(=O)—.
A specific value for X is —O—C(=O)—NR$_a$— or —NR$_a$—C(=O)—O—.

A specific value for X is —O—C(=O)—O—.
A specific value for X is —NR$_a$—C(=O)—NR$_a$—.

In one embodiment of the invention, when a compound is shown with a wedged (up) or dashed (back) bond the compound may be enriched by about 60%, 80%, 90%, 95%, 98%, or 99% in the absolute stereoisomer represented.

In one embodiment of the invention ring A is an aromatic ring and $R^5$ is absent.

In one embodiment the invention provides a compound of the following formula

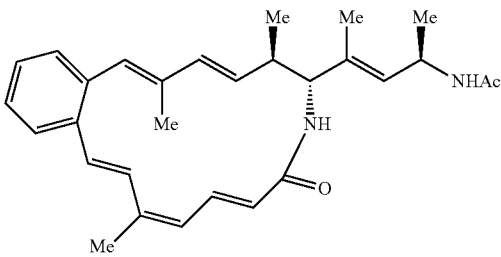 [SMILES: CC(=O)N[C@H](C)/C=C(\C)[C@@H]1NC(=O)/C=C/C=C(C)\C=C\c2ccccc2/C=C(C)/C=C/[C@H]1C]

or a salt thereof, which can be made using procedures similar to those described herein.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are tosylate, methanesulfonate, acetate, citrate, malonate, tartarate, succinate, benzoate, ascorbate, α-ketoglutarate, and α-glycerophosphate salts. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid. Alkali metal (for example, sodium, potassium or lithium) or alkaline earth metal (for example calcium) salts of carboxylic acids can also be made.

The compounds of the present invention can also contain unnatural proportions of atomic isotopes at one or more of the atoms that constitute such compounds. For example, the present invention also embraces isotopically-labeled variants of the present invention which are identical to those recited herein, but for the fact that one or more atoms are replaced by an atom having the atomic mass or mass number different from the predominant atomic mass or mass number usually found in nature for the atom. All isotopes of any particular atom or element as specified are contemplated within the scope of the compounds of the invention, and their uses. Exemplary isotopes that can be incorporated in to compounds of the invention include isotopes of hydrogen, carbon, nitrogen, oxygen, phosphorous, sulfur, fluorine, chlorine and iodine, such as $^2$H ("D"), $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically labeled compounds of the present invention (e.g., those labeled with $^3$H or $^{14}$C) are useful in compound and/or substrate tissue distribution assays. Tritiated ($^3$H) and carbon-14 ($^{14}$C) isotopes are useful for their ease of preparation and detectability. Further substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$, and $^{18}F$ are useful for positron emission tomography (PET) studies to examine substrate receptor occupancy. Isotopically labeled compounds of the present inventions can generally be prepared by following procedures analogous to those disclosed in the Schemes and/or in the Examples herein below, by substituting an isotopically labeled reagent for a non-isotopically labeled reagent.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Processes for preparing compounds of formula I are provided as further embodiments of the invention and are illustrated by the following procedures in which the meanings of the generic radicals are as given above unless otherwise qualified.

pared as described in Scheme 1. The synthesis of this compound allowed the interaction between the natural product and the receptor to be studied and provided important information regarding the structure-activity-relationship and pharmacophore identification.

Scheme 1 outlines the retrosynthetic analysis of truncated superstolide A (3). Sequential disconnections reveal fragments 4, 5 and 6 as potential key intermediates, with Suzuki, Negishi, and Stille couplings playing roles in the synthetic strategy.

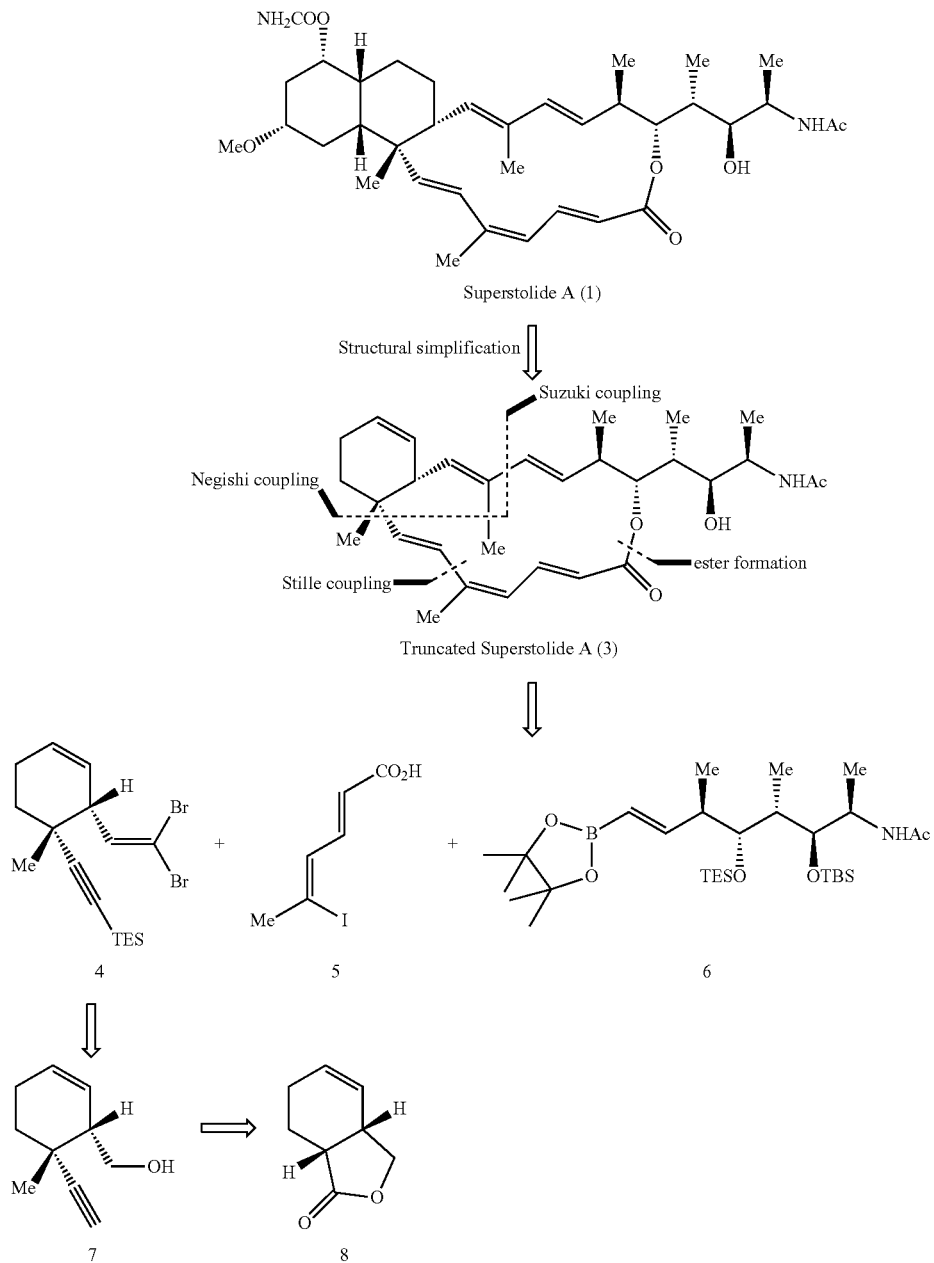

A truncated superstolide A (3) in which the cis-fused functionalized decalin is simplified to a cyclohexene ring whereas the 16-membered macrolactone remains intact has been pre- Scheme 2 illustrates the preparation of compound 4. The starting material lactone 8 was prepared enantioselectively in 73% yield (95% ee) employing an elegant Diels-Alder reaction (see Ward, D. E.; Santos, M. S. *Org. Lett.* 2005, 7, 3533). Lactone 8 was treated with LDA followed by quenching the resulting enolate with MeI to provide compound 11 in 95% yield with the requisite stereochemistry at the quaternary carbon. DIBAL reduction followed by the addition of lithiotrimethylsilyldiazomethane to lactol 12 gave alkyne 7 in 88% yield (see Ohira, S.; Okai, K.; Moritani, T. *J. Chem. Soc. Chem. Commun.* 1992, 92, 721). Compound 7 reacted with 2.5 equivalents of n-BuLi to afford a dianion that was quenched with 3 equivalents of TESOTf to furnish an intermediate, which was treated with 5% HCl to chemoselectively cleave the TES silyl ether to provide compound 13 in 86% yield. Homoallylic alcohol 13 was carefully oxidized to its corresponding aldehyde 14, which was immediately converted to geminal dibromo compound 4 in 72% yield.

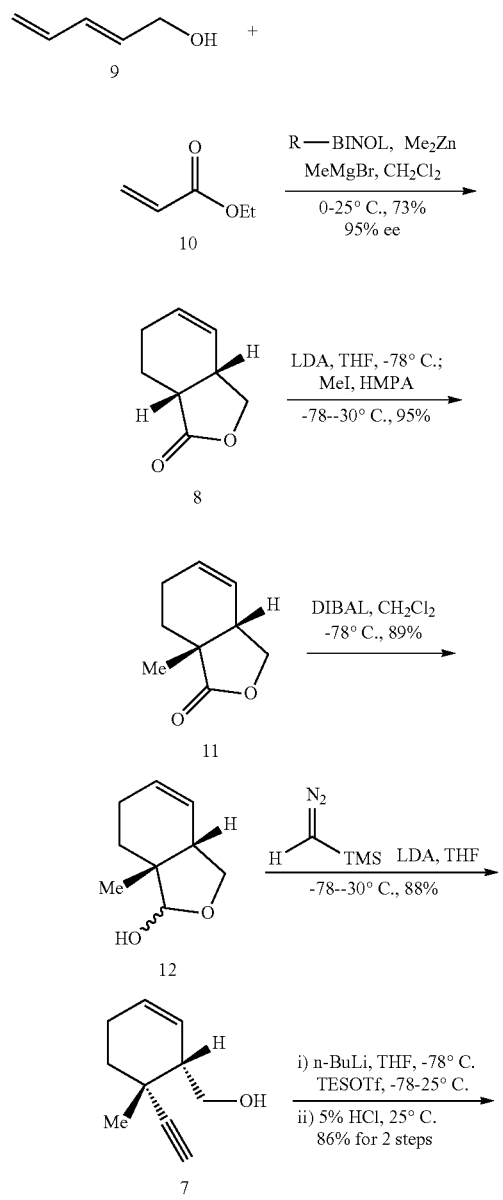

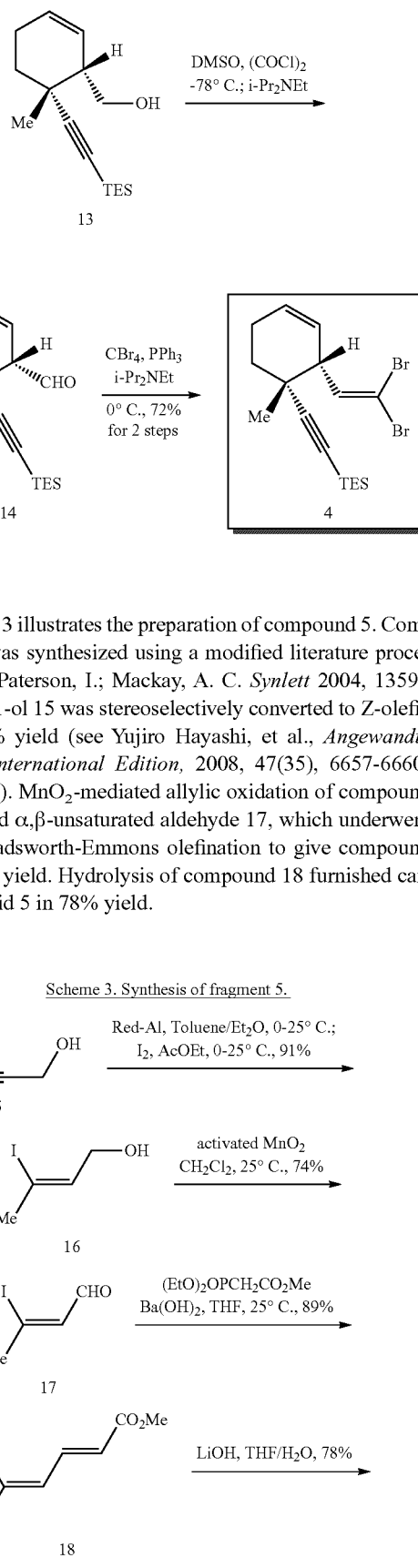

Scheme 3 illustrates the preparation of compound 5. Compound 5 was synthesized using a modified literature procedure (see Paterson, I.; Mackay, A. C. *Synlett* 2004, 1359). But-2-yn-1-ol 15 was stereoselectively converted to Z-olefin 16 in 91% yield (see Yujiro Hayashi, et al., *Angewandte Chemie, International Edition*, 2008, 47(35), 6657-6660) (Scheme 3). MnO$_2$-mediated allylic oxidation of compound 16 afforded α,β-unsaturated aldehyde 17, which underwent Horner-Wadsworth-Emmons olefination to give compound 18 in 89% yield. Hydrolysis of compound 18 furnished carboxylic acid 5 in 78% yield.

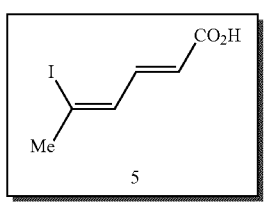

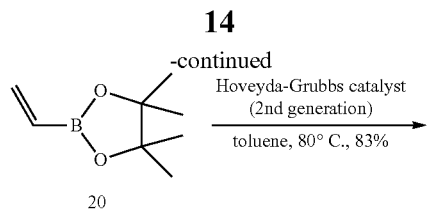

Scheme 4 illustrates the preparation of compound 6. The cross-metathesis between olefin 19 and pinacol vinylboronate 20 proved to be challenging (see D'Auria, M. V. et al., *J. Am. Chem. Soc.* 1994, 116, 6658) (Scheme 4). After much experimentation, it was discovered that employing the second generation of Grubbs-Hoveyda catalyst olefin 19 was successfully converted to trans-vinyl borane 6 in 83% yield (see Christie Morrill and Robert H. Grubbs, *J. Org. Chem.,* 2003, 68, 6031-6034).

Scheme 5 illustrates the preparation of compound 3. Suzuki coupling between geminal dibromo compound 4 and vinyl borane 6 provided compound 21 in 70% yield with complete stereoselectivity (see Akira Suzuki, *J. Organomet. Chem.* 1997, 576, 147) (Scheme 5). Negishi coupling between vinyl bromide 21 and Me$_2$Zn gave the requisite trisubstituted olefin 22 in 86% yield with complete stereoselectivity (see Ei-ichi Negishi, et al., *Aldrichimica Acta,* 2005, 38, 71). It should be noted that the triethyl silyl group attached to the alkyne moiety of compound 21 was important because it prevented the facile cyclic carbopalladation followed by cross coupling, a major side reaction that competed with the Negishi coupling (see Ei-ichi Negishi, et al., *Tetrahedron Lett.* 1990, 31, 4393).

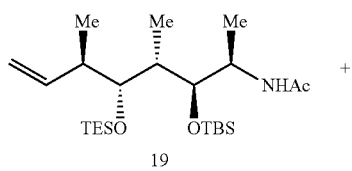

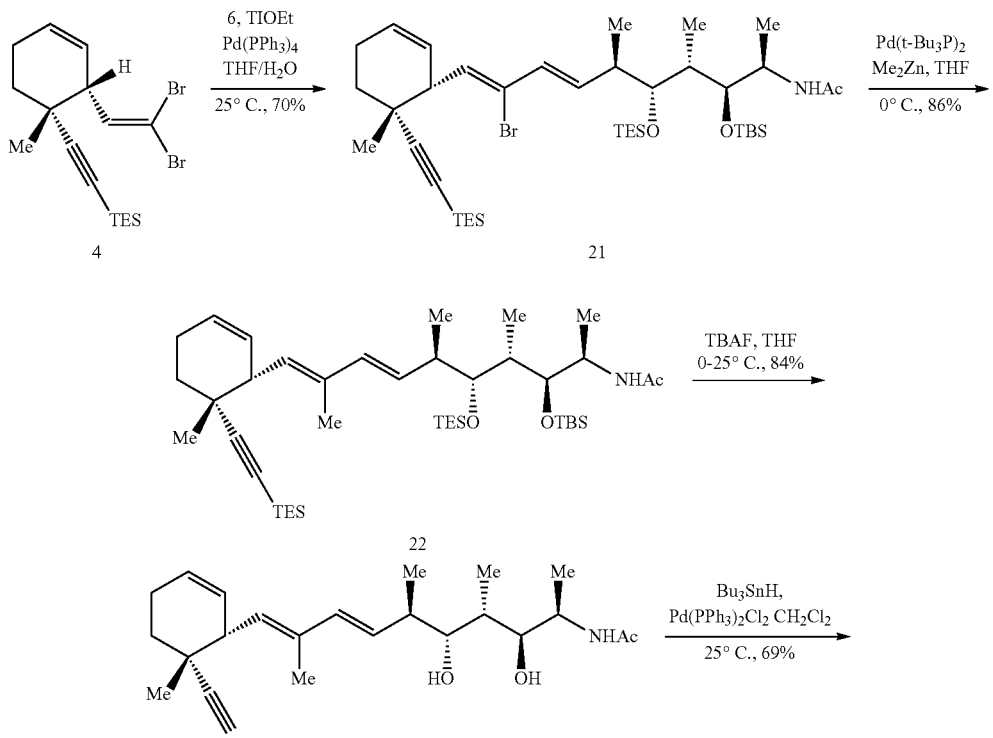

-continued

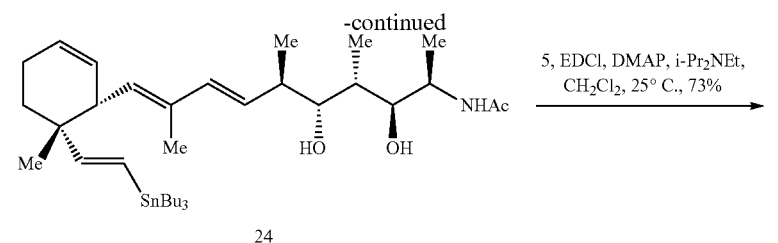

24

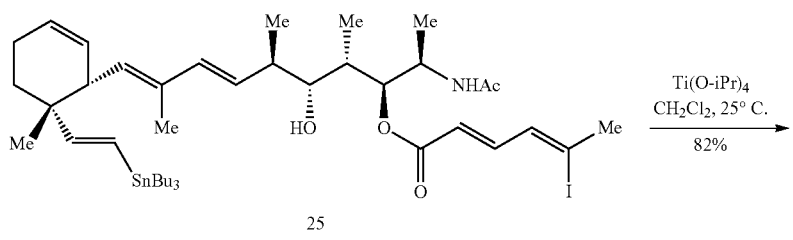

25

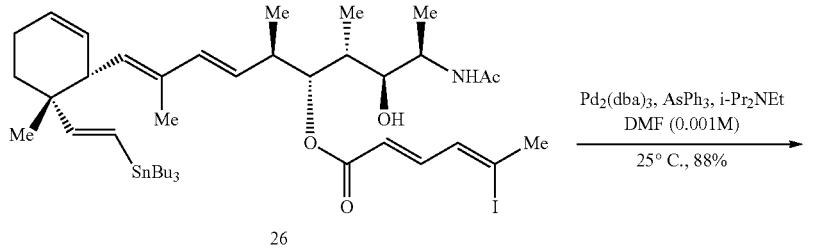

26

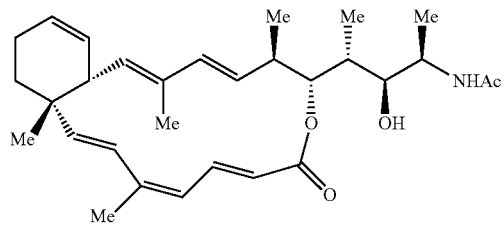

3

Three silyl protecting groups were removed by TBAF to afford alkyne 23 in 84% yield, which underwent a regio and stereoselective hydrostannylation to furnish vinyl stannane 24 in 69% yield. Regioselective esterification between alcohol 24 and carboxylic acid 5 provided compound 25, which was isomerized to the desired ester 26 upon treatment with Ti(O-iPr)$_4$. Finally, compound 24 underwent a very clean intramolecular Stille coupling to give truncated superstolide A (3) in 88% yield (see John K. Stille, *Angew. Chem. Int. Ed. Engl.*, 1986, 25, 508-524).

Alternatively, compound 25 can be converted to compound 3 as illustrated in Scheme 6.

Scheme 6. Alternative conversion of Compound 25 to Compound 3

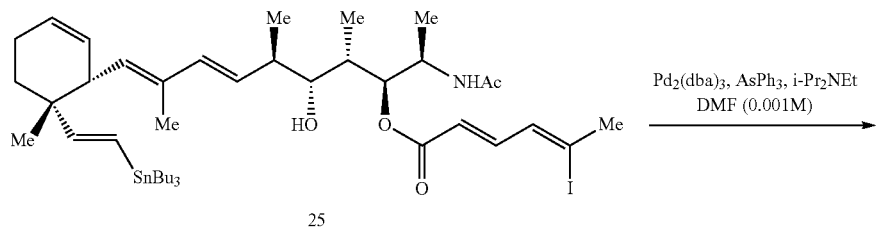

25

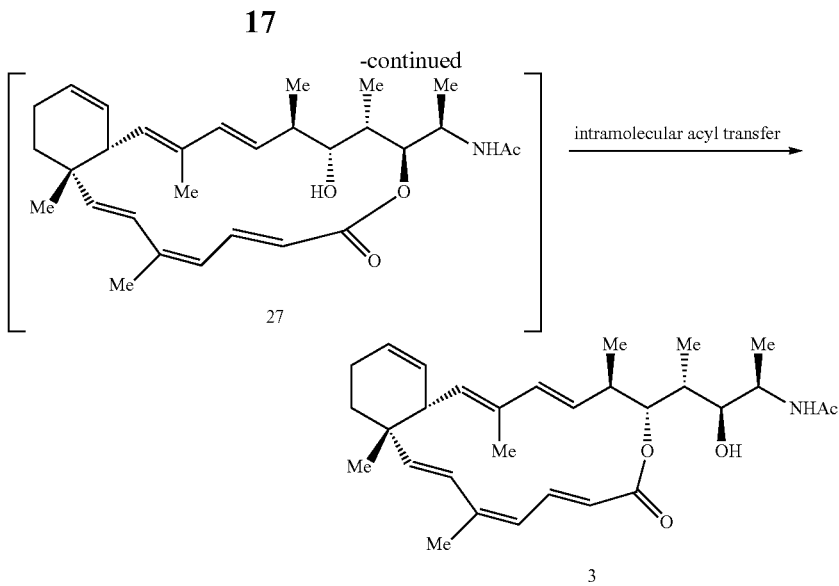

As illustrated in Scheme 6, compound 25 can undergo intramolecular Stille coupling to form an 18-membered macrolactone 27, which will undergo an intramolecular acyl transfer to directly give compound 3.

The truncated superstolide A (3) was successfully synthesized in only 14 steps from commercially available starting material (E)-penta-2,4-dien-1-ol 9 in 6.2% overall yield. It should be noted that all stereogenic carbons and double bonds present in the target molecule were constructed stereospecifically. Furthermore, this convergent synthetic strategy demonstrates once again the highly versatile palladium-catalyzed cross-coupling reactions in the synthesis of complex molecules.

The anti-cancer activity of a compound may be determined using pharmacological models which are well known to the art, or using the assays described below.

Cell Viability Assay: The antiproliferative effect of compound 3 was determined by performing 3-(4,5-dimethylthiazol-2-yl)-2,5-diphenyltetrazolim (MTT) assay. Briefly, cancer cells at varying concentrations—2,000 cells/well (A375SM, MEL624 and SK-MEL-2,) and 5,000 cells/well (HT29, H1299, and HCT116, Raji, and HL-60)—were seeded onto a 96-well plate in triplicates. Following an overnight incubation, the cells were treated with log-scale serially increasing concentrations of compound 3 for 72 hours at 37° C. At the end of the 72 hours period, cells were treated with the MTT reagent (Sigma-Aldrich, M O) and the antiproliferative effect of compound 3 was measured as previously described (Zhou Y, Achanta G, Pelicano H, Gandhi V, Plunkett W, and Huang P (2002). *Molecular Pharmacology* 61:222-229). The $IC_{50}$ values correspond to a concentration of compound 3 that inhibits cell viability by 50%.

The antiproliferative effect of compound 3 was evaluated in two human colon carcinoma cell lines (HT29, HCT116), three malignant melanoma cell lines (A375SM, MEL624, and SK-MEL-2), one human non-small cell lung carcinoma cell line (H1299), one lymphoma cell line (Raji), one leukemia cell line (HL-60), and one malignant breast cancer cell line (MDA-MB231) using MTT assay. The data (MTT curves and $IC_{50}$ tables) are shown in FIG. 1 and in the following Table 1.

TABLE 1

Antiproliferative effect of 3 on various malignant tumor cells[a]

| Entry | Cell Line | $IC_{50}$ (nM) |
|---|---|---|
| 1 | HT29 | 7.54 |
| 2 | A375SM | 36.52 |
| 3 | MEL624 | 53.06 |
| 4 | SK-MEL-2 | 63.82 |
| 5 | H1299 | 56.75 |
| 6 | HCT116 | 52.71 |
| 7 | Raji | 76.73 |
| 8 | HL60 | 11.85 |
| 9 | MDA-MB231 | 18 |

[a]These cells were treated with log-scale serial diluted concentrations of truncated superstolide A (3) from 1 to 3000 nM for 72 hours and the effect of truncated superstolide A (3) on cell death was measured by performing a MTT assay.

Compound 3 is about seven times more potent in suppressing tumor cell proliferation than its parent natural product superstolide A in HT-29 cell (the $IC_{50}$ value for superstolide A in HT-29 is 64 nm). In addition, compound 3 is also highly potent ($IC_{50}$ in 10-70 nM) in suppressing tumor cell proliferation in the other eight tested cell lines. These results confirm that the 16-membered macrolactone is the pharmacophore that interacts with its putative target in the cells, and the modification of the functionalized cis-decalin to a cyclohexene ring does not significantly affect anticancer activity.

In conclusion, a simplified superstolide A analogue that maintains superstolide A's original potent anticancer activity has been identified. The enantioselective synthesis employed is highly efficient, convergent and flexible. Accordingly, it can be used to prepare other compounds of formula (I).

The invention also provides novel intermediate compounds (e.g. a compound selected from compounds 4-27) disclosed herein that are useful for preparing compounds of formula I as well as methods for preparing such novel intermediate compounds and methods for preparing a compound of formula I using such novel intermediate compounds.

Compounds of the invention can also be prepared as illustrated in the following Schemes 7-8.

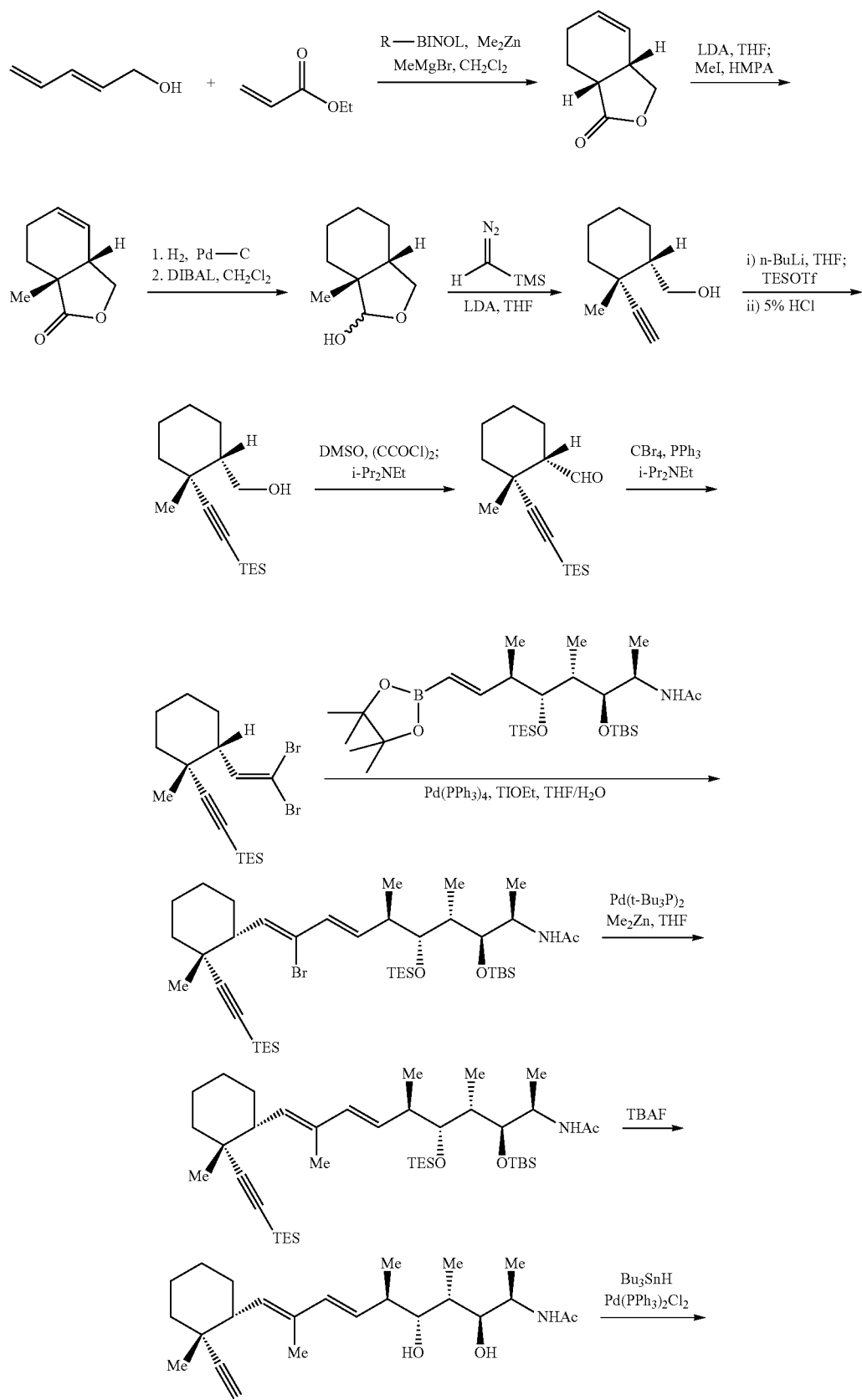
Scheme 7

-continued
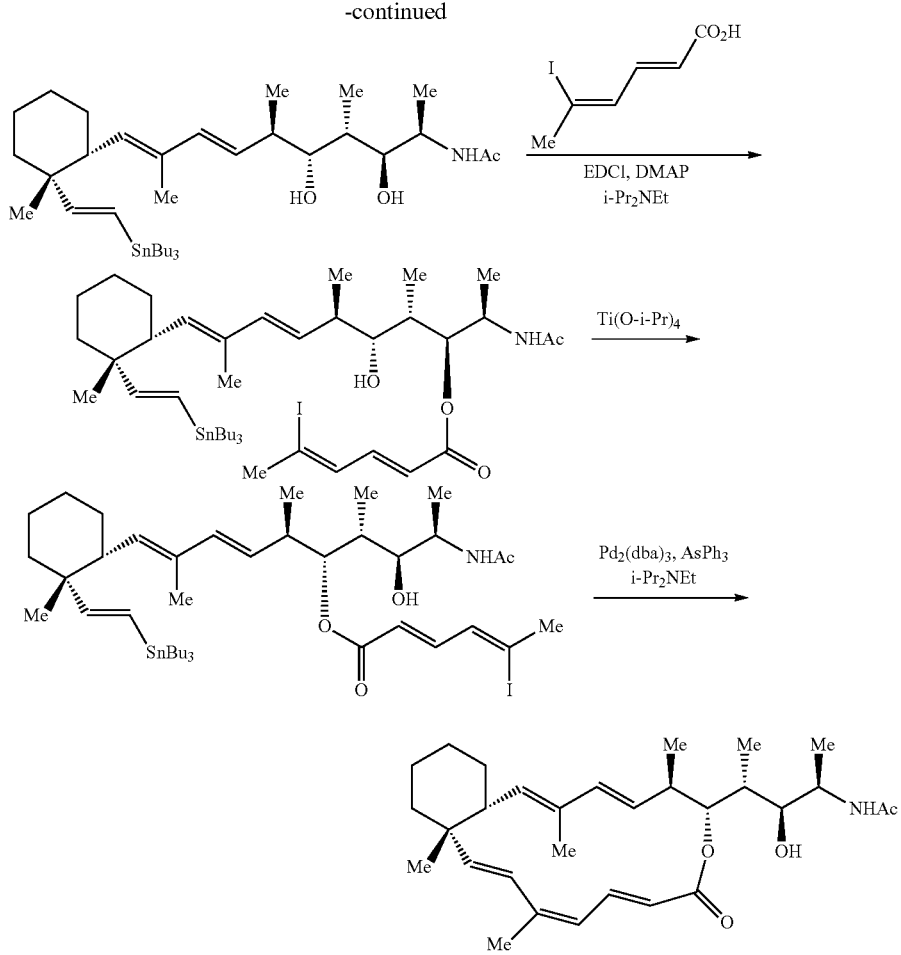
Scheme 8
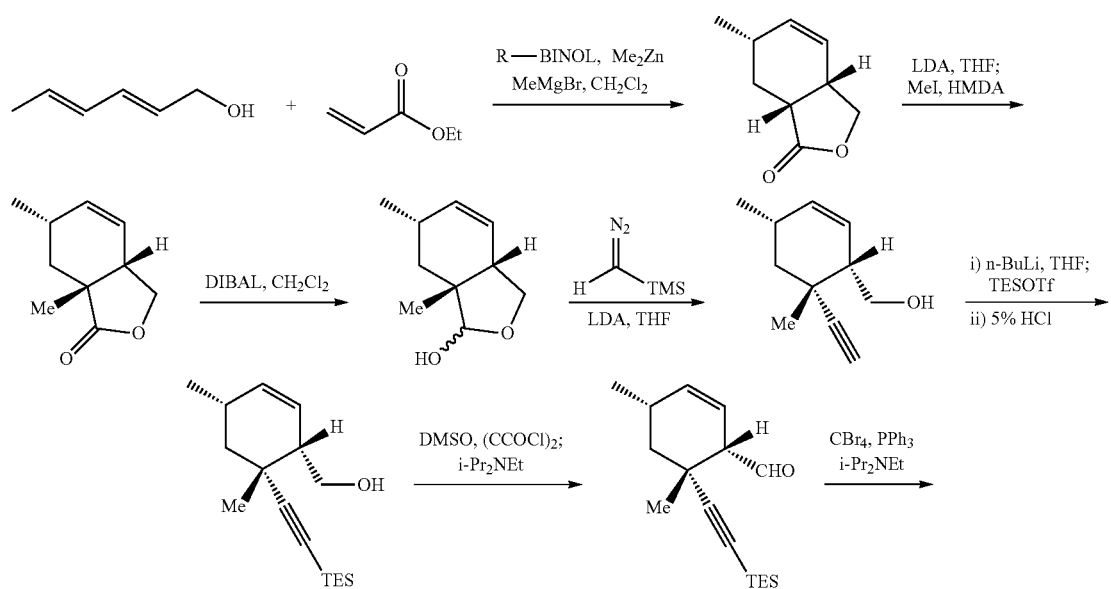

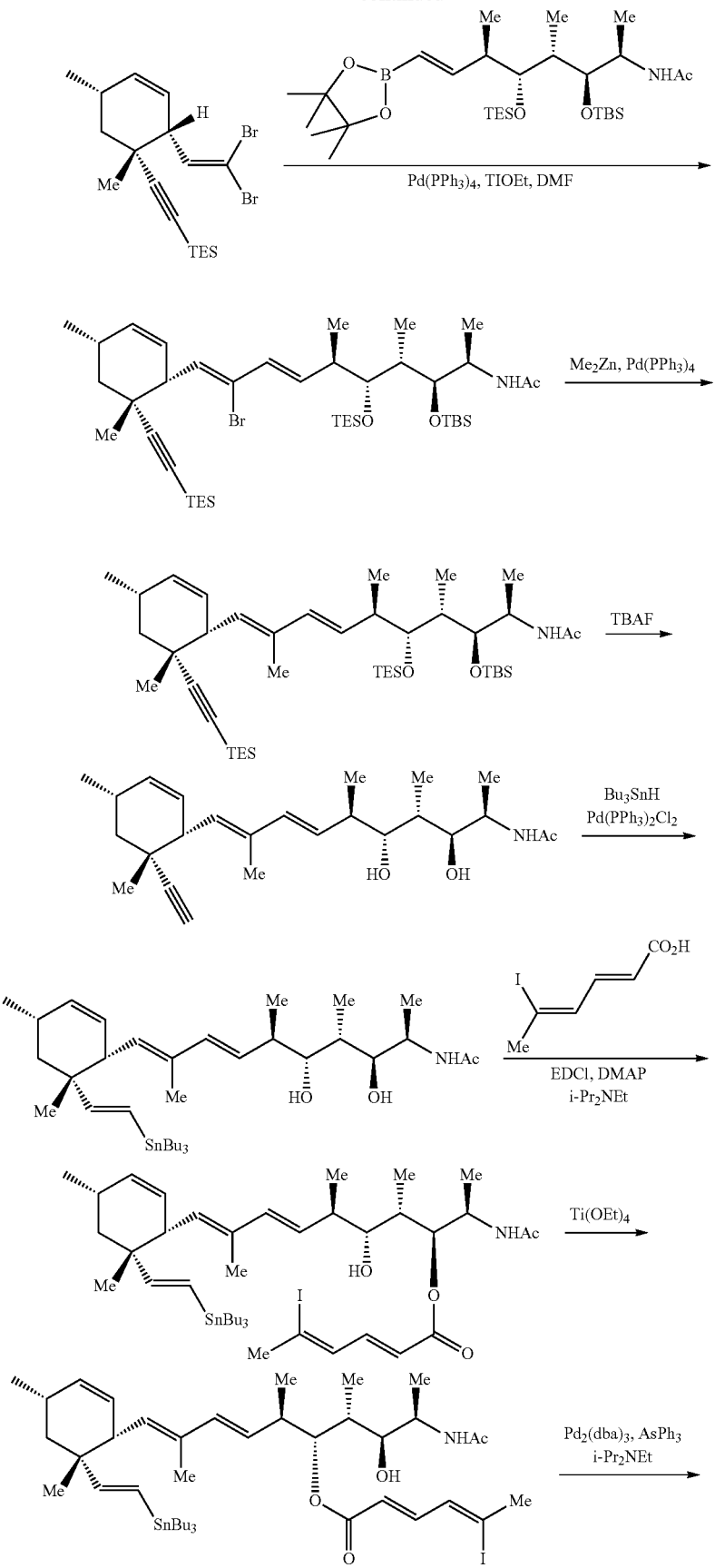

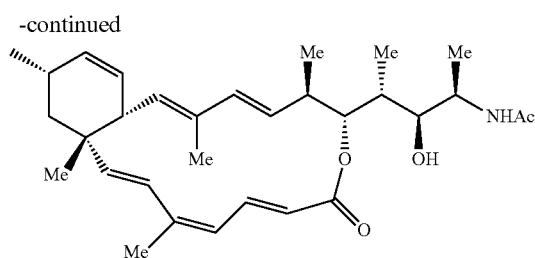

The invention also provides novel processes and novel intermediate compounds described herein (e.g. novel processes and novel intermediate compounds illustrated in Schemes 1-8) that are useful for preparing compounds of formula I.

In one embodiment the invention provides a method for preparing a compound of formula I comprising converting a corresponding compound of formula 100 to the compound of formula I:

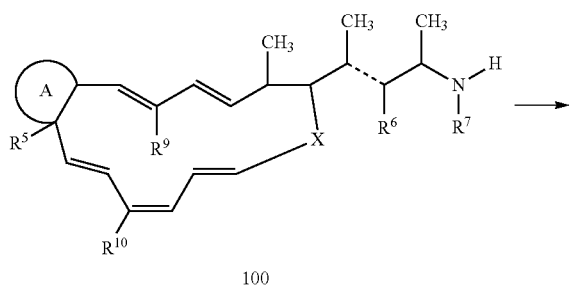

In one embodiment the invention provides a method comprising converting a compound of formula 104 to a compound of formula 119:

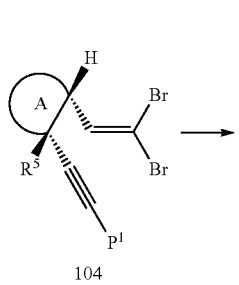

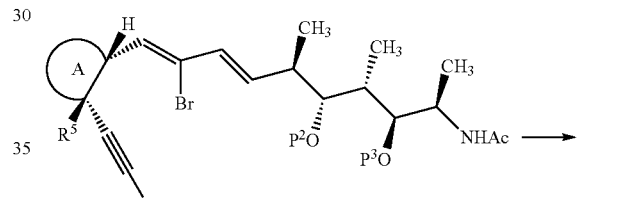

In one embodiment the invention provides a method comprising converting a compound of formula 119 to a compound of formula 120:

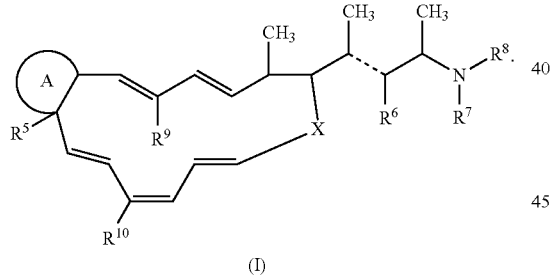

In one embodiment the invention provides a method comprising converting a compound of formula 124 to a compound of formula 103:

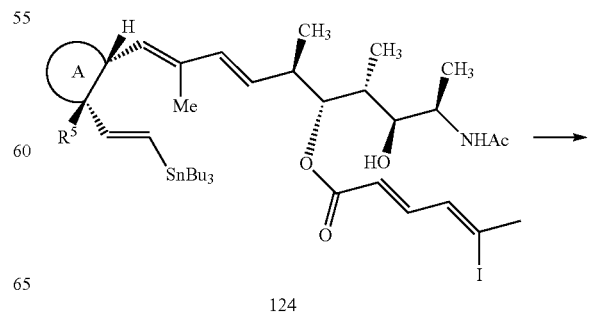

-continued

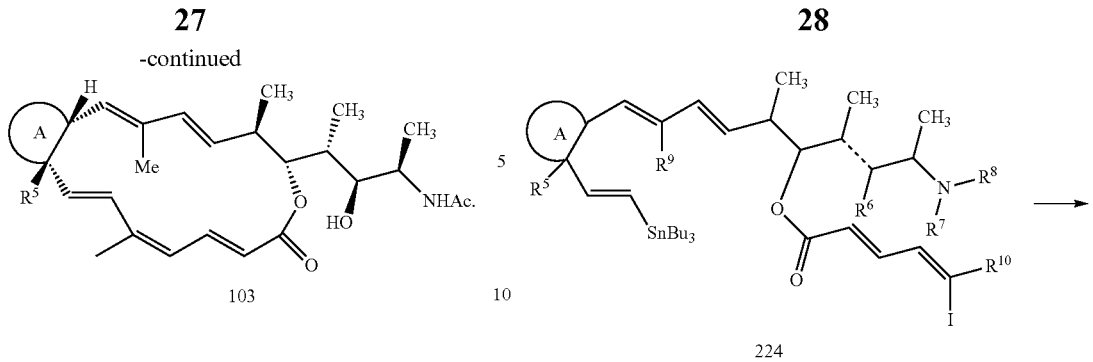

103

224

In one embodiment the invention provides a method comprising converting a compound of formula 204 to a compound of formula 219:

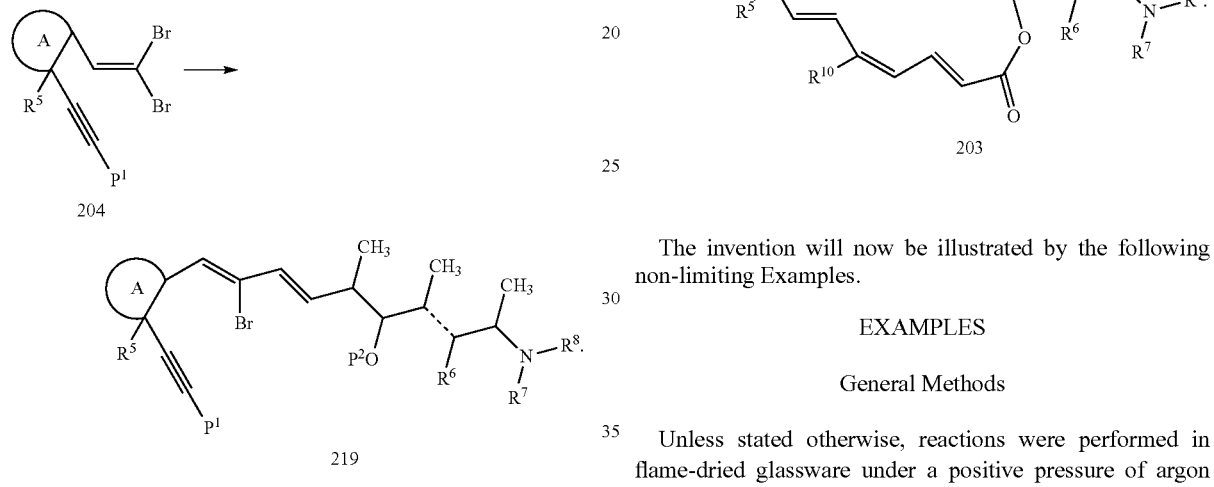

204

219

In one embodiment the invention provides a method comprising converting a compound of formula 219 to a compound of formula 220:

219

220

In one embodiment the invention provides a method comprising converting a compound of formula 224 to a compound of formula 203:

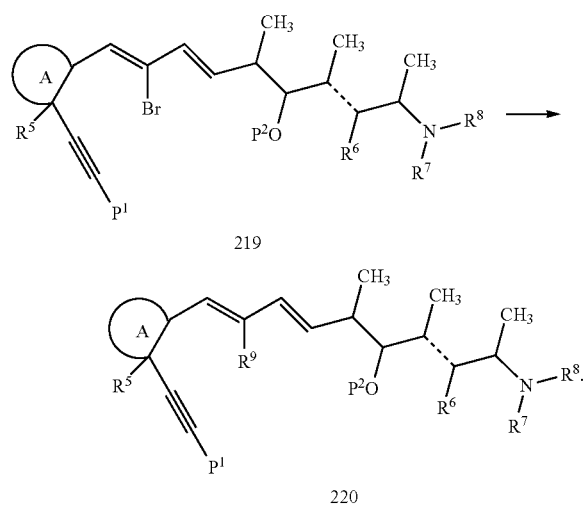

203

The invention will now be illustrated by the following non-limiting Examples.

EXAMPLES

General Methods

Unless stated otherwise, reactions were performed in flame-dried glassware under a positive pressure of argon using freshly distilled solvent. Tetrahydrofuran (THF) and diethyl ether were distilled from sodium/benzophenone before use. Dichloromethane and toluene were distilled from $CaH_2$. Anhydrous methanol (99.8%) was bought from Aldrich. Thin-layer chromatography (TLC) was performed using Dynamic Adsorbents silica gel w/h F-254 250 µm glass plates. Visualization of the developed chromatography was performed by UV absorbance (254 nm) and visualizing solutions. The commonly employed TLC visualizing stains were: anisaldehyde solution and 12-molybdophosphoric acid solution. Column chromatography was performed using Dynamic absorbents silica gel (32-63 µm). All $^1$H-NMR and $^{13}$C-NMR spectra were recorded with a Bruker Advance300 (300 MHz). In reported $^1$H NMR spectra, data are presented as follows: chemical shift (in ppm on the δ scale relative to δ H 7.26 for the residual protons in $CDCl_3$ and δ H 7.16 for the residual protons in $C_6D_6$), integration, multiplicity (s=singlet, d=doublet, t=triplet, q=quartet, m=multiplet, br=broad), coupling constant (J/Hz). Coupling constants were taken directly from the spectra and are uncorrected. In reported $^{13}$C NMR spectra, all chemical shift values are reported in ppm on the δ scale, with an internal reference of δ C 77.16 for $CDCl_3$ and δ C 128.06 for $C_6D_6$. Mass spectral determinations were carried out by using electrospray ionization as ionization source (ESI). Optical rotations were measured on Jasco P-1020 polarimeters. Melting points are uncorrected.

ABBREVIATIONS (R)-(+)-BINOL (R)-(+)-1,1'-Bi-2-naphthol
DIBAL-H=diisobutylaluminum hydride
DMAP=4-Dimethylaminopyridine
DMF=Dimethylformamide
DMSO=Dimethyl sulfoxide
EDCI=1-Ethyl-3-(3-dimethylaminopropyl)carbodiimide
HMPA=hexamethylphosphoramide
Pd$_2$(dba)$_3$=Tris(dibenzylideneacetone)dipalladium(0)
TBAF=tetra-n-butylammonium fluoride
TBS32 tert-butyldimethylsilyl
TESOTf=triethylsilyl trifluoromethanesulfonate
TES=Triethylsilyl Example 1

Preparation of Compound 3

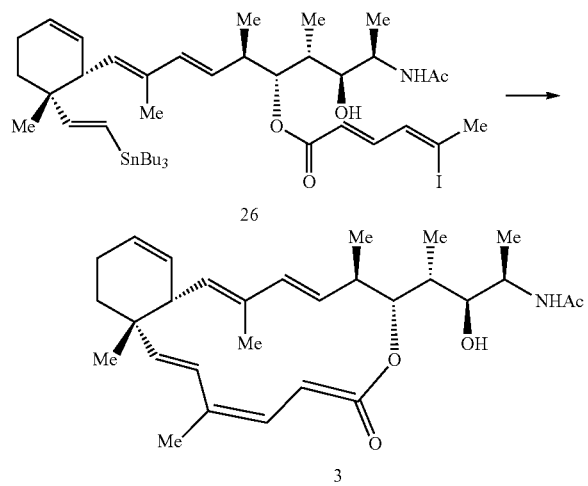

To a solution of the ester 26 (38 mg, 42.3 μmol) in DMF (42 mL) was added i-Pr$_2$NEt (76 μL), AsPh$_3$ (10 mg, 33.6 μmol) and Pd$_2$(dba)$_3$ (8 mg, 8.74 μmol) and the reaction mixture was degassed by three freeze-thaw cycles. After that, the flask was covered with aluminum foil and the reaction mixture was stirred at room temperature for 8 hrs. The DMF was removed at a high vacuum rotavapor and the residue was purified by prep. TLC affording final lactone 3 (18 mg) as a white solid in 88% yield.

Data for compound 3: $[\alpha]_D^{23}$=+192.0 (c=0.91 in CHCl$_3$); $^1$H NMR (300 MHz, CDCl$_3$) δ 7.08 (1H, dd, J=10.8, 15.3 Hz), 6.54 (1H, dd, J=15.3 Hz), 6.17 (1H, d, J=15.3 Hz), 6.13 (1H, d, J=8.4 Hz), 5.81 (1H, d, J=11.1 Hz), 5.60 (1H, d, J=12.3 Hz), 5.56 (1H, d, J=16.5 Hz), 5.55-5.50 (1H, m), 5.39-5.36 (1H, m), 5.33 (1H, d, J=10.5 Hz), 5.18 (1H, dd, J=10.5, 15.3 Hz), 4.70 (1H, 0.9, 10.5 Hz), 4.51 (1H, d, J=3.9 Hz), 4.10-4.06 (1H, m), 3.04 (1H, ddd, J=2.7, 4.2, 10.5 Hz), 2.86 (1H, dd, J=5.4, 9.9 Hz), 2.64-2.55 (1H, m), 2.02 (2H, br), 1.86 (3H, s), 1.80 (3H, s), 1.73-1.61 (2H, m), 1.67 (3H, s), 1.31-1.23 (1H, m), 0.99 (3H, s), 0.97 (3H, d, J=7.2 Hz), 0.95 (3H, d, J=7.2 Hz), 0.77 (3H, d, J=6.9 Hz); $^{13}$C NMR (75 MHz, CDCl$_3$) δ 169.8, 169.0, 144.5, 143.7, 139.7, 137.0, 134.3, 130.7, 128.9, 127.7, 125.6, 125.0, 124.3, 120.2, 73.1, 45.4, 42.4, 40.4, 38.0, 37.5, 28.9, 26.1, 23.6, 22.8, 21.4, 18.0, 12.7, 12.6, 8.82; HR-MS (ESI): calcd for C$_{30}$H$_{43}$NO$_4$Na$^+$ [M+Na$^+$]: 504.3084. found: 504.3087.

Intermediate ester 26 was prepared as follows.

a. Preparation of Compound 5

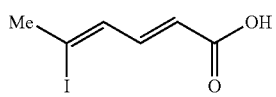

Data for compound 5: $^1$H NMR (300 MHz, CDCl$_3$) δ 7.43 (1H, dd, J=10.2, 15.3 Hz), 6.31 (1H, d, J=10.5 Hz), 6.03 (1H, d, J=15.3 Hz), 2.72 (3H, s); $^{13}$C NMR (75 MHz, CDCl$_3$) δ 172.0, 148.4, 132.6, 122.2, 113.6, 35.0; HR-MS (ESI): calcd for C$_6$H$_6$O$_2$I$^-$ [M−H$^+$]: 236.9407. found: 236.9414.

b. Preparation of Compound 6

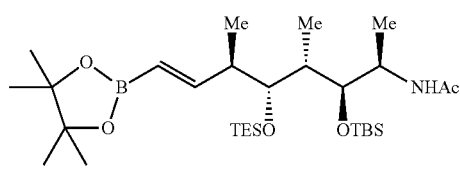

To a solution of olefin 19 (200 mg, 0.44 mmol) and vinylboronic acid pinacol ester (120 μL, 0.71 mmol) in dried toluene (2 mL) at 80° C. was added a solution of Hoveyda-Grubbs 2$^{nd}$ catalyst (28 mg, 44.6 μmol) in toluene (2 mL) dropwise. Second batch of vinylboronic acid pinacol ester (120 μL, 0.71 mmol) was added to the reaction mixture, followed by dropwise addition of second batch of Hoveyda-Grubbs 2$^{nd}$ catalyst (12 mg, 19.2 μmol) in toluene (1 mL) After completing addition of Hoveyda-Grubbs catalyst, the reaction mixture was stirred at 80° C. and cooled to r.t. The solvent was removed on a rotary evaporator and the residue was purified by flash chromatography (hexanes/EtOAc=5:1–3:1) to give 6 (213 mg) as light yellow oil in 83% yield. Data for compound 6: $[\alpha]_D^{23}$=33.5 (c=0.82 in CH$_2$Cl$_2$); $^1$H NMR (300 MHz, CDCl$_3$) δ 6.55 (1H, dd, J=7.5, 18.0 Hz), 5.47 (1H, d, J=7.2 Hz), 5.36 (1H, d, J=18.0 Hz), 3.97-3.92 (1H, m), 3.59-3.56 (2H, m), 2.51-2.40 (1H, m), 1.83 (3H, s), 1.68-1.56 (1H, m), 1.15 (12H, s), 0.81 (9H, s), 0.98-0.83 (18H, m), 0.57 (3H, d, J=8.1 Hz), 0.52 (3H, d, J=7.8 Hz), −0.07 (6H, s); $^{13}$C NMR (75 MHz, CDCl$_3$) δ 168.3, 156.0, 83.0, 76.7, 75.5, 46.9, 44.9, 41.7, 26.0, 24.8, 24.7, 23.6, 18.3, 16.5, 15.7, 7.21, 5.62, −3.65, −4.57; HR-MS (ESI): calcd for C$_{30}$H$_{62}$NO$_5$NaSi$_2^+$ [M+Na$^+$]: 606.4152. found: 606.4171.

c. Preparation of Compound 8

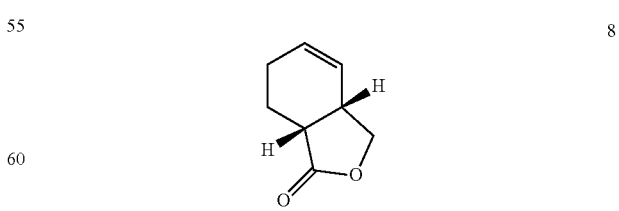

Me$_2$Zn (9.46 mL, 2 M in toluene, 18.9 mmol) was added to a stirred solution of dienol 9 (1.59 g, 18.9 mmol) in CH$_2$Cl$_2$ (95 mL) at 0° C. under argon. MeMgBr (6.28 mL, 3 M in ethyl ether, 18.9 mmol) was added to a stirred solution of (R)-(+)-

BINOL (5.41 g, 18.9 mmol) in CH$_2$Cl$_2$ (95 mL) at 0° C. under argon. After 5 min, the Me$_2$Zn solution was added to the MeMgBr solution at 0° C. under argon. After 5 min, the mixture was diluted with CH$_2$Cl$_2$ (760 mL CH$_2$Cl$_2$ was added, concentration of dienol 9: 0.02 M) and then methyl acrylate (25.7 mL, 283.8 mmol) was added. The reaction mixture was allowed to warm to room temperature, and after the indicated time, was quenched by addition of saturated aqueous NaHCO$_3$ (ca. 2 mL). The resulting mixture was passed through a short column of Na$_2$SO$_4$ and Celite and the combined eluate and washings were concentrated. The chiral ligand (R)-BINOL had almost same R$_f$ value as the desired product. Therefore, it is necessary to transform the (R)-BINOL to its disilyl ether using TESOTf/NEt$_3$ before purification. The residual oil was dissolved in CH$_2$Cl$_2$ (100 mL) and to the above solution, NEt$_3$ (6.59 mL, 47.3 mmol) and TESOTf (9.40 mL, 41.6 mmol) was added respectively at 0° C. The reaction mixture was allowed to warm to room temperature, quenched with saturated aqueous NaHCO$_3$ (10 mL). The organic phase was separated, and the aqueous phase was extracted with CH$_2$Cl$_2$ (10 mL×3). The combined organic layers were washed with brine, dried over Na$_2$SO$_4$, concentrated, and purified by flash chromatography (hexanes/EtOAc=10:1-5:1) to give lactone 8 (1.85 g) as colorless oil in 73% yield. Data for compound 8: $[\alpha]_D^{23}$=−117.0 (c=1.00 in CHCl$_3$); $^1$H NMR (300 MHz, CDCl$_3$) δ 5.96-5.91 (1H, m), 5.61 (1H, dd, J=2.4, 9.9 Hz), 4.37 (1H, dd, J=6.3, 8.7 Hz), 4.05 (1H, dd, J=2.4, 8.7 Hz), 3.11-3.05 (1H, m), 2.87-2.82 (1H, m), 2.12-1.93 (3H, m), 1.86-1.72 (1H, m); $^{13}$C NMR (75 MHz, CDCl$_3$) δ 178.8, 130.7, 125.3, 72.2, 38.1, 35.3, 21.0, 19.7.

d. Preparation of Compound 11

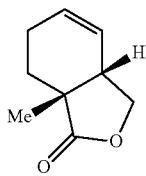

11

To a solution of diisopropylamine (1.89 mL, 10.8 mmol) in THF (15 mL) was added a solution of n-BuLi (4.32 mL, 2.5 M in hexane, 10.9 mmol) at −30° C. After the reaction mixture was stirred at −30° C. for 15 min and cooled to −78° C., the solution of lactone 8 (1.0 g, 7.24 mmol) in THF (20 mL) was cannulated to the above solution. The light yellow solution was warmed up to −30° C. in 30 min and cooled to −78° C. again. After HMPA (1.88 mL, 10.8 mmol) and MeI (0.9 mL, 14.5 mmol) were added sequentially at −78° C., the reaction mixture was allowed to warm to room temperature, quenched with saturated aqueous NaHCO$_3$ (5 mL) and diluted with EtOAc (20 mL). The organic phase was separated, and the aqueous phase was extracted with EtOAc (5 mL×3). The combined organic layers were washed with brine, dried over Na$_2$SO$_4$, concentrated, and purified by flash chromatography (hexanes/EtOAc=5:1) to give α-methyl lactone 11 (1.05 g) as colorless oil in 95% yield. Data for compound 11: $[\alpha]_D^{23}$=−113.9 (c=1.43 in CHCl$_3$); $^1$H NMR (300 MHz, CDCl$_3$) δ 5.94-5.88 (1H, m), 5.63-5.58 (1H, m), 4.46 (1H, dd, J=7.2, 9.0 Hz), 3.94 (1H, dd, J=4.5, 8.7 Hz), 2.70-2.66 (1H, m), 2.10-2.03 (2H, m), 1.91 (1H, ddd, J=5.7, 5.7, 13.2 Hz), 1.55 (1H, ddd, J=6.6, 6.9, 13.5 Hz), 1.27 (3H, s); $^{13}$C NMR (75 MHz, CDCl$_3$) δ 181.4, 129.5, 124.7, 70.9, 42.3, 40.9, 27.4, 22.0, 21.4; HR-MS (ESI): calcd for C$_9$H$_{13}$O$_2^+$ [M+H$^+$]: 153.0910. found: 153.0913.

e. Preparation of Compound 12

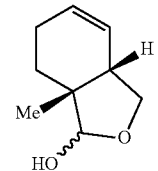

12

To a solution of lactone 11 (1.1 g, 7.24 mmol) in CH$_2$Cl$_2$ (25 mL) at −78° C. under argon atmosphere was added a solution of DIBAL-H (7.9 mL, 1.0 M in CH$_2$Cl$_2$, 7.9 mmol) dropwise. After stirring at −78° C. for 25 min, the reaction was quenched by adding saturated aqueous NaHCO$_3$ dropwise (1 mL) at −78° C. The resulting mixture was diluted with CH$_2$Cl$_2$ (100 mL), and saturated aqueous potassium sodium tartrate (50 mL) was added. The mixture was stirred vigorously for 1 hr. The organic phase was separated and the aqueous layer was extracted with CH$_2$Cl$_2$ (20 mL×3). The combined organic layers were washed with brine, dried over Na$_2$SO$_4$, concentrated, and purified by flash chromatography (hexanes/EtOAc=2/1) to give compound 12 (992 mg) as white foam in 89% yield.

Data for compound 12 (mixture of two diastereomers 1:0.22): $^1$H NMR (300 MHz, CDCl$_3$) δ 5.77 5.70 (1.22H, m), 5.66-5.55 (1.22H, m), 5.09 (0.22H, d, J=5.7 Hz), 4.95 (1H, d, J=2.7 Hz), 4.27 (1H, dd, J=8.1, 9.0 Hz), 4.02 (0.22H, dd, J=8.1, 8.4 Hz), 3.62 (0.22H, dd, J=8.1, 9.6 Hz), 3.53 (1H, dd, J=8.1, 8.4 Hz), 2.55-2.48 (1H, m), 2.41-2.33 (0.22H, m), 2.13-1.99 (2H+0.44H, m), 1.69-1.31 (2H+0.44H, m), 1.03 (3H+0.66H, s); $^{13}$C NMR (75 MHz, CDCl$_3$) for the major isomer δ 126.9, 125.4, 104.8, 73.2, 43.2, 42.1, 27.8, 21.8, 17.5; $^{13}$C NMR (75 MHz, CDCl$_3$) for the minor isomer δ 128.2, 124.6, 106.7, 71.5, 44.9, 41.1, 22.8, 22.1, 21.6. HR-MS (ESI): calcd for C$_9$H$_{13}$O$_2^-$ [M−H$^+$]: 153.0910. found: 153.0913.

f. Preparation of Compound 7

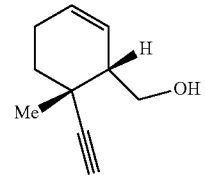

7

To a solution of diisopropylamine (4.28 mL, 30.5 mmol) in THF (50 mL) was added a solution of n-BuLi (12.2 mL, 2.5 M in hexane, 30.5 mmol) at −30° C. After the reaction mixture was stirred at −30° C. for 15 min and cooled to −78° C., the solution of (trimethylsilyl)diazomethane (7.64 mL, 2.0 M in diethyl ether, 15.3 mmol) was added to the above solution. The light yellow solution was warmed up to −50° C. in 20 min and cooled to −78° C. again. After the solution of compound 12 (1.57 g, 10.2 mmol) in THF (10 mL) were added at −78° C., the reaction was allowed to warm to room temperature, quenched with saturated aqueous NaHCO$_3$ (5 mL) and diluted with CH$_2$Cl$_2$ (20 mL). The organic phase was separated, and the aqueous phase was extracted with CH$_2$Cl$_2$ (5 mL×3). The combined organic layers were washed with brine, dried over $Na_2SO_4$, concentrated, and purified by flash chromatography (hexanes/EtOAc=3:1) to give acetylene 7 (1.34 g) as pale yellow oil in 88% yield. Data for compound 7: $[\alpha]_D^{23}$=+99.3 (c=1.12 in $CHCl_3$); $^1$H NMR (300 MHz, $CDCl_3$) δ 5.78-5.72 (1H, m), 5.57 (1H, ddd, J=2.4, 4.5, 10.2 Hz), 3.81 (3.81, dd, J=5.4, 11.7 Hz), 3.68 (1H, dd, J=5.7, 10.8 Hz), 2.60 (1H, br), 2.27-2.16 (1H, m), 2.11 (1H, s), 2.09-2.04 (1H, m), 2.01-1.91 (1H, m), 1.76-1.70 (1H, m), 1.50 (1H, ddd, J=3.9, 5.4, 14.7 Hz), 1.28 (3H, m); $^{13}$C NMR (75 MHz, $CDCl_3$) δ 127.6, 126.2, 89.2, 70.1, 64.1, 47.3, 34.8, 32.0, 27.9, 22.8; HR-MS (ESI): calcd for $C_{10}H_{15}O^+$ [M+H$^+$]: 151.1117. found: 151.1112.

g. Preparation of Compounds 13a and 13

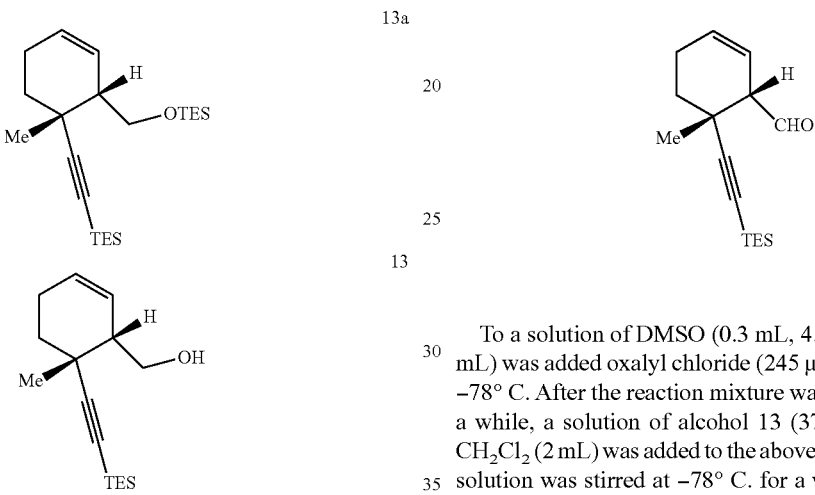

To a solution of compound 7 (502 mg, 3.34 mmol) in THF (10 mL) at −78° C. under argon atmosphere was added a solution of n-BuLi (4.28 mL, 2.5 M in hexane, 10.7 mmol) dropwise. After stirring at −78° C. for 15 min, TESOTf (1.89 mL, 8.35 mmol) was added to the above reaction solution at −78° C. The reaction mixture was allowed to warm to room temperature, quenched with saturated aqueous $NaHCO_3$ (5 mL) and diluted with EtOAc (20 mL). The organic phase was separated, and the aqueous phase was extracted with EtOAc (5 mL×3). The combined organic layers were washed with brine, dried over $Na_2SO_4$ and concentrated. The crude di-TES protected compound 13a was redissolved in THF/15% aq HCl (10 mL/2 mL). The above solution was stirred at room temperature for 15 min, quenched with saturated aqueous $NaHCO_3$ (5 mL) and diluted with EtOAc (60 mL). The organic phase was separated, and the aqueous phase was extracted with EtOAc (5 mL×3). The combined organic layers were washed with brine, dried over $Na_2SO_4$, concentrated, and purified by flash chromatography (hexanes/EtOAc=3:1) to give alcohol 13 (760 mg) as colorless oil in 86% yield for 2 steps. Data for compound 13a: $[\alpha]_D^{24}$=+45.7 (c=0.92 in $CH_2Cl_2$); $^1$H NMR (300 MHz, $CDCl_3$) δ 5.75-5.65 (2H, m), 3.99 (1H, dd, J=4.8, 9.6 Hz), 3.54 (1H, dd, J=9.6, 9.6 Hz), 2.34 (1H, m), 2.11-2.07 (1H, m), 1.99-1.90 (1H, m), 1.72 (1H, ddd, J=2.7, 5.4, 12.6 Hz), 1.49 (1H, ddd, J=5.1, 10.8, 12.6 Hz), 1.31 (3H, s), 0.97 (9H, t, J=7.8 Hz), 0.96 (9H, t, J=7.8 Hz), 0.61 (6H, q, J=7.8 Hz), 0.53 (6H, q, J=7.8 Hz); $^{13}$C NMR (75 MHz, $CDCl_3$) δ 126.8, 126.7, 111.9, 82.2, 64.6, 47.4, 36.0, 33.2, 28.5, 23.3, 7.53, 6.83, 4.66, 4.43; HR-MS (ESI): calcd for $C_{22}H_{43}OSi_2^+$ [M+H$^+$]: 379.2847. found: 379.2838. Data for compound 13: $[\alpha]_D^{23}$=+65.9 (c=1.02 in $CHCl_3$); $^1$H NMR (300 MHz, $CDCl_3$) δ 5.81-5.75 (1H, m), 5.58 (1H, ddd, J=2.1, 2.4, 9.9 Hz), 3.79 (2H, d, J=5.4 Hz), 2.71 (1H, br), 2.31-2.18 (1H, m), 2.13-2.08 (1H, m), 2.04-1.93 (1H, m), 1.78 (1H, ddd, J=2.4, 2.4, 12.9 Hz), 1.55 (1H, ddd, J=2.4, 2.4, 13.2 Hz), 1.31 (3H, s), 0.96 (9H, t, J=7.8 Hz), 0.56 (6H, q, J=7.8 Hz); $^{13}$C NMR (75 MHz, $CDCl_3$) δ 127.7, 126.2, 113.8, 83.5, 64.2, 47.7, 34.6, 32.8, 27.8, 22.8, 7.43, 4.47; HR-MS (ESI): calcd for $C_{16}H_{29}OSi^+$ [M+H$^+$]: 265.1982. found: 265.1975.

h. Preparation of Compound 14

To a solution of DMSO (0.3 mL, 4.2 mmol) in $CH_2Cl_2$ (5 mL) was added oxalyl chloride (245 µL, 98%, 2.80 mmol) at −78° C. After the reaction mixture was stirred at −78° C. for a while, a solution of alcohol 13 (370 mg, 1.40 mmol) in $CH_2Cl_2$ (2 mL) was added to the above solution. The resulting solution was stirred at −78° C. for a while and diisopropylethyl amine was added. The reaction mixture was allowed to warm to room temperature, quenched with saturated aqueous $NaHCO_3$ (5 mL) and diluted with $CH_2Cl_2$ (20 mL) The organic phase was separated, and the aqueous phase was extracted with $CH_2Cl_2$ (5 mL×3). The combined organic layers were washed with brine, dried over $Na_2SO_4$, concentrated under vacuum at 0° C. to give aldehyde 14 solution in $CH_2Cl_2$ (3 mL), which was used directly in next step without purification. Data for compound 14: $^1$H NMR (300 MHz, $CDCl_3$) δ 9.67 (1H, d, J=2.7 Hz), 5.85-5.82 (1H, m), 5.46-5.42 (1H, m), 2.60-2.58 (1H, m), 2.28-2.20 (1H, m), 2.01-1.92 (2H, m), 1.77-1.69 (1H, m), 1.51-1.42 (1H, m), 1.25 (3H, s), 0.84 (9H, q, J=7.8 Hz), 0.51-0.38 (6H, t, J=7.8 Hz); HR-MS (ESI): calcd for $C_{16}H_{27}OSi^+$ [M+H$^+$]: 263.1826. found: 263.1831.

i. Preparation of Compound 4

To a solution of $PPh_3$ (2.93 g, 11.2 mmol) in $CH_2Cl_2$ (5 mL) was added $CBr_4$ (1.85 g, 5.6 mmol) at 0° C. After the reaction mixture was stirred at 0° C. for a while and diisopropylethylamine (2.19 mL, 12.6 mmol) was added. The resulting dark orange mixture was stirred at 0° C. for a while and the solution of aldehyde 14 in CH$_2$Cl$_2$ (2 mL) were added. Stirred at 0° C. for 10 min, the reaction was quenched with saturated aqueous NaHCO$_3$ (5 mL) and diluted with CH$_2$Cl$_2$ (20 mL) The organic phase was separated, and the aqueous phase was extracted with CH$_2$Cl$_2$ (5 mL×3). The combined organic layers were washed with brine, dried over Na$_2$SO$_4$, concentrated, and purified by flash chromatography (hexanes/EtOAc=3:1) to give dibromo compound 4 (421 mg) as light yellow oil in 72% yield for two steps. Data for compound 4: $[\alpha]_D^{23}$=+23.9 (c=0.91 in CHCl$_3$); $^1$H NMR (300 MHz, CDCl$_3$) δ 6.60 (1H, d, J=9.9 Hz), 5.82-5.76 (1H, m), 5.31 (1H, ddd, J=2.4, 4.2, 9.9 Hz), 2.92 (1H, ddd, J=2.4, 3.6, 9.9 Hz), 2.39-2.31 (1H, m), 2.10-1.98 (1H, m), 1.82 (1H, ddd, J=2.7, 3.0, 12.9 Hz), 1.55 (1H, ddd, J=5.4, 10.5, 12.9 Hz), 1.26 (3H, s), 0.99 (9H, t, J=7.8 Hz), 0.58 (6H, q, J=7.8 Hz); $^{13}$C NMR (75 MHz, CDCl$_3$) δ 140.1, 128.5, 125.1, 111.5, 89.5, 83.7, 50.5, 35.1, 34.8, 28.1, 23.5, 7.70, 4.75; HR-MS (ESI): calcd for C$_{17}$H$_{27}$SiBr$_2^+$ [M+H$^+$]: 417.0243. found: 417.0238.

j. Preparation of Compound 21

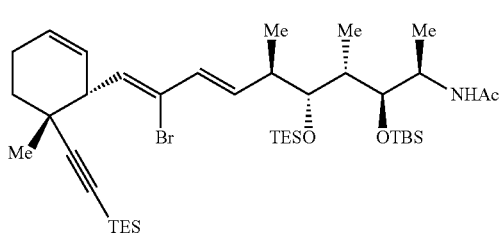

To a stirred solution of dibromoolefin 4 (182 mg, 0.44 mmol), Pd(PPh$_3$)$_4$ (25 mg, 22 µmol) and vinyl boronic ester 6 (272 mg, 0.47 mmol) in degassed THF/H$_2$O (2.4 mL/0.8 mL) at room temperature was added thalliumethylate (87 mg, 0.35 mmol). After stirring at room temperature for a while, another batch of thalliumethylate (130 mg, 0.52 mmol) was added. The reaction mixture was stirred at room temperature for a while and diluted with EtOAc (50 mL) and H$_2$O (15 mL) The solid was removed by filtration through Celite. The organic layer was separated and the aqueous was extracted twice with EtOAc (20 mL). The combined organic layers were dried over Na$_2$SO$_4$, filtered and concentrated in vacuum. Purification via column chromatography (hexane/ethyl acetate 20:1) yielded compound 21 (242 mg, 70%) as a colorless oil film. Data for compound 21: $[\alpha]_D^{23}$=+19.7 (c=1.83 in CHCl$_3$); $^1$H NMR (300 MHz, CDCl$_3$) δ 6.18-6.02 (3H, m), 5.76-5.71 (1H, m), 5.53 (1H, d, J=15.9 Hz), 5.27 (1H, dd, J=1.8, 9.6 Hz), 4.04-3.99 (1H, m), 3.73 (1H, dd, J=2.1, 6.3 Hz), 3.63 (1H, dd, J=3.3, 6.9 Hz), 3.27-3.22 (1H, m), 2.70-2.62 (1H, m), 2.45-2.33 (1H, m), 2.06-1.96 (1H, m), 1.94 (3H, s), 1.83-1.69 (2H, m), 1.54 (1H, ddd, J=5.1, 11.7, 12.9 Hz), 1.19 (3H, s), 1.09 (3H, d, J=6.6 Hz), 1.08 (3H, d, J=6.6 Hz), 1.01-0.92 (21H, m), 0.91 (9H, s), 0.65 (6H, dt, J=0.6, 7.8 Hz), 0.55 (6H, dt, J=0.6, 8.1 Hz), 0.03-0.01 (6H, m); $^{13}$C NMR (75 MHz, CDCl$_3$) δ 168.5, 137.3, 133.6, 129.9, 127.7, 126.75, 126.73, 112.1, 82.9, 77.7, 74.9, 49.0, 47.1, 42.3, 41.2, 35.6, 35.5, 28.3, 26.1, 23.8, 23.7, 18.5, 18.4, 15.7, 7.75, 7.34, 5.82, 4.83, −3.72, −4.53; HR-MS (ESI): calcd for C$_{41}$H$_{76}$NO$_3$NaSi$_3$Br$^+$ [M+Na$^+$]: 816.4209. found: 816.4222.

k. Preparation of Compound 22

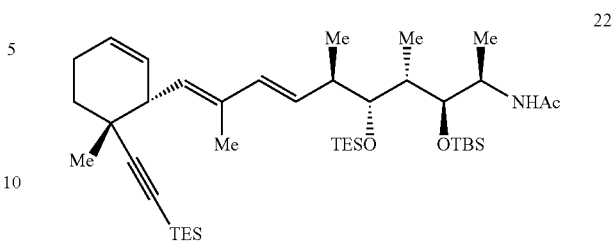

To a solution of Pd(t-Bu$_3$P)$_2$ (2 mg, 4.1 µmol) in degassed THF (0.60 mL) was added a solution of ZnMe$_2$ (200 µL, 1.2 M in toluene, 241 µmol) at 0° C. This solution was cannulated into a flask of neat bromo bromoolefin 21 (64 mg, 80.5 µmol) at 0° C. Stirred at 0° C. for 4.5 hrs, the reaction was quenched with saturated aqueous NaHCO$_3$ (5 mL) and diluted with CH$_2$Cl$_2$ (20 mL) The organic phase was separated, and the aqueous phase was extracted with CH$_2$Cl$_2$ (5 mL×3). The combined organic layers were washed with brine, dried over Na$_2$SO$_4$, concentrated, and purified by flash chromatography (hexanes/EtOAc=3:1) to give compound 22 (51 mg) as colorless oil in 86% yield. Data for compound 22: $[\alpha]_D^{23}$=+17.3 (c=0.74 in CHCl$_3$); $^1$H NMR (300 MHz, CDCl$_3$) δ 6.11 (1H, d, J=15.9 Hz), 5.64 (1H, dd, J=8.7, 15.9 Hz), 5.73-5.55 (3H, m), 5.25 (1H, d, J=9.9 Hz), 4.10-3.95 (1H, m), 3.74 (1H, dd, J=2.4, 6.3 Hz), 3.64 (1H, dd, J=3.0, 6.9 Hz), 2.91 (1H, d, J=9.9 Hz), 2.60-2.32 (2H, m), 2.06 (3H, s), 1.86-1.70 (3H, m), 1.76 (3H, d, J=0.9 Hz), 1.58-1.50 (1H, m), 1.15 (3H, s), 1.10 (3H, d, J=6.9 Hz), 1.08 (3H, d, J=7.2 Hz), 1.00 (9H, t, J=8.1 Hz), 0.99 (9H, t, J=8.1 Hz), 0.94-0.89 (3H, m), 0.92 (9H, s), 0.67 (6H, q, J=8.1 Hz), 0.56 (6H, q, J=8.1 Hz), 0.05 (3H, s), 0.02 (3H, s); $^{13}$C NMR (75 MHz, CDCl$_3$) δ 168.3, 135.5, 134.5, 132.2, 129.4, 128.6, 126.9, 112.2, 82.3, 77.6, 74.9, 46.9, 45.0, 41.9, 41.8, 35.8, 28.1, 25.9, 23.8, 23.5, 18.4, 18.3, 15.8, 13.0, 11.5, 7.60, 7.19, 5.67, 4.72, −3.94, −4.70; HR-MS (ESI): calcd for C$_{42}$H$_{79}$NO$_3$NaSi$_3^+$ [M+Na$^+$]: 752.5260. found: 752.5249.

l. Preparation of Compound 23

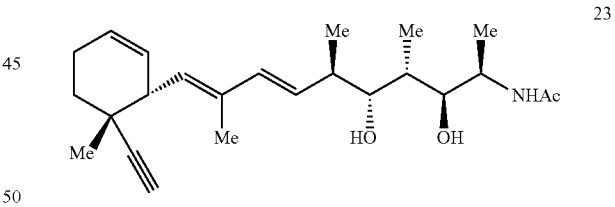

To a stirred solution of silylether 22 (157 mg, 214 µmol) in THF (4 mL) was added a solution of TBAF (0.65 mL, 1 M in THF, 0.65 mmol) at 0° C. The reaction was gradually warmed up to 25° C. and stirred for 2 hrs, the reaction was quenched with saturated aqueous NaHCO$_3$ (5 mL) and diluted with CH$_2$Cl$_2$ (20 mL). The organic phase was separated, and the aqueous phase was extracted with CH$_2$Cl$_2$ (5 mL×3). The combined organic layers were washed with brine, dried over Na$_2$SO$_4$, concentrated, and purified by flash chromatography (CH$_2$Cl$_2$/MeOH=30:1-20:1) to give diol 23 (70 mg) as colorless oil in 84% yield. Data for compound 23: $[\alpha]_D^{23}$=+50.3 (c=1.07 in CHCl$_3$); $^1$H NMR (300 MHz, CDCl$_3$) δ 6.28 (1H, d, J=15.6 Hz), 5.86 (1H, d, J=9.0 Hz), 5.79-5.74 (1H, m), 5.64 (1H, d, J=10.2 Hz), 5.42 (1H, dd, J=9.0, 15.6 Hz), 5.33-5.28 (1H, m), 4.24-4.12 (1H, m), 3.73 (1H, dd, J=2.1, 9.6 Hz), 3.53 (1H, br), 3.41 (1H, br), 2.94 (1H, ddd, J=2.4, 3.6, 10.2 Hz), 2.41-2.27 (2H, m), 2.12-2.03 (1H, m), 2.10 (1H, s), 1.99 (3H, s), 1.90-1.82 (2H, m), 1.79 (3H, d, J=1.2 Hz), 1.57 (1H, ddd, J=8.7, 11.1, 12.6 Hz), 1.21 (3H, s), 1.19 (3H, d, J=6.6 Hz), 0.98 (3H, d, J=4.2 Hz), 0.96 (3H, d, J=4.2 Hz); $^{13}$C NMR (75 MHz, CDCl$_3$) δ 169.2, 137.8, 134.2, 133.1, 129.9, 128.2, 127.1, 88.2, 77.6, 74.0, 69.7, 47.1, 44.6, 41.8, 35.2, 35.1, 34.7, 28.1, 23.6, 23.4, 16.7, 15.3, 13.1, 9.92; calcd for C$_{24}$H$_{38}$NO$_3{}^+$ [M+H$^+$]: 388.2846. found: 388.2852.

m. Preparation of Compound 24

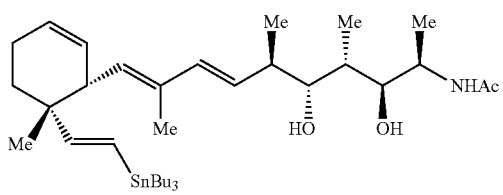

To a stirred solution of alkyne 23 (70 mg, 0.18 mmol) and Pd(PPh$_3$)$_2$Cl$_2$ (19 mg, 27 µmol) in degassed CH$_2$Cl$_2$ (2 mL) was added Bu$_3$SnH (73 µL, 0.27 mmol) at room temperature. After 5 min, another batch of Bu$_3$SnH (49 pt, 0.18 mmol) was added. Stirred at room temperature for 1 hr, the reaction was quenched with saturated aqueous NaHCO$_3$ (5 mL) and diluted with CH$_2$Cl$_2$ (20 mL). The organic phase was separated, and the aqueous phase was extracted with CH$_2$Cl$_2$ (5 mL×3). The combined organic layers were washed with brine, dried over Na$_2$SO$_4$, concentrated, and purified by flash chromatography (CH$_2$Cl$_2$/MeOH=50:1-30:1) to give vinyl stannane 24 (85 mg) as colorless oil in 69% yield. Data for compound 24: [α]$_D{}^{23}$=+83.2 (c=0.88 in CHCl$_3$); $^1$H NMR (300 MHz, CDCl$_3$) δ 6.04 (1H, d, J=15.6 Hz), 5.95 (1H, d, J=19.5 Hz), 5.75 (1H, d, J=19.5 Hz), 5.65-5.57 (2H, m), 5.31-5.16 (3H, m), 4.13-4.01 (1H, m), 3.58 (1H, d, J=9.3 Hz), 3.40 (1H, dd, J=6.6, 12.3 Hz), 3.16 (1H, d, J=6.6 Hz), 2.81-2.76 (1H, m), 2.23-2.07 (1H, m), 2.05-1.93 (1H, m), 1.87 (3H, s), 1.82 (1H, br), 1.75-1.71 (1H, m), 1.65 (3H, d, J=0.9 Hz), 1.52-1.32 (8H, m), 1.25-1.13 (8H, m), 1.08 (3H, d, J=6.6 Hz), 0.91-0.71 (24H, m); $^{13}$C NMR (75 MHz, CDCl$_3$) δ 169.2, 154.7, 138.3, 134.5, 132.7, 129.1, 128.7, 126.6, 123.9, 78.0, 74.0, 47.2, 44.6, 42.0, 40.7, 35.1, 32.7, 29.3, 27.4, 25.2, 23.7, 23.2, 16.8, 15.5, 13.9, 13.0, 10.0, 9.66. HR-MS (ESI): calcd for C$_{36}$H$_{65}$NO$_3$NaSn$^+$ [M+Na$^+$]: 702.3879. found: 702.3884.

n. Preparation of Compound 25

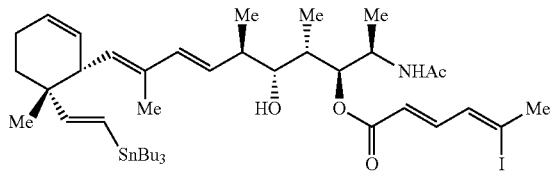

To a stirred solution of diol 24 (55 mg, 81.1 µmol), unsaturated acid 5 (24 mg, 101.4 µmol), EDCI (39 mg, 202.8 µmol) and i-Pr$_2$NEt (70 µL, 0.41 mmol) in CH$_2$Cl$_2$ (1 mL) was added a solution of DMAP (25 mg, 202.8 µmol) in CH$_2$Cl$_2$ at room temperature. Stirred at room temperature for 8 hrs, the reaction was quenched with saturated aqueous NaHCO$_3$ (2 mL) and diluted with CH$_2$Cl$_2$ (10 mL) The organic phase was separated, and the aqueous phase was extracted with CH$_2$Cl$_2$ (5 mL×3). The combined organic layers were washed with brine, dried over Na$_2$SO$_4$, concentrated, and purified by flash chromatography (hexanes/EtOAc=1:1-1:2) to give ester 25 (53 mg) as colorless oil in 73% yield.

Data for compound 25: [α]$_D{}^{23}$=+26.2 (c=1.38 in CHCl$_3$); $^1$H NMR (300 MHz, CDCl$_3$) δ 7.29 (1H, dd, J=10.2, 15.0 Hz), 6.19 (1H, d, J=10.5 Hz), 6.10 (1H, d, J=8.1 Hz), 6.01 (1H, d, J=5.4 Hz), 5.98 (1H, d, J=3.6 Hz), 5.94 (1H, d, J=2.4 Hz), 5.75 (1H, d, J=19.5 Hz), 5.60-5.56 (1H, m), 5.33 (1H, dd, J=8.4, 15.6 Hz), 5.30-5.26 (1H, m), 5.15 (1H, d, J=10.2 Hz), 4.93 (1H, dd, J=1.8, 9.6 Hz), 4.28-4.24 (1H, m), 3.17 (1H, d, J=10.2, 9.6 Hz), 2.81-2.76 (1H, m), 2.61 (3H, s), 2.20-2.12 (1H, m), 2.06-1.85 (3H, m), 1.85 (3H, s), 1.83-1.78 (1H, m), 1.64 (3H, d, J=0.6 Hz), 1.48-1.32 (8H, m), 1.24-1.12 (6H, m), 1.04 (3H, d, J=6.9 Hz), 0.90-0.71 (24H, m); $^{13}$C NMR (75 MHz, CDCl$_3$) δ 169.3, 167.6, 154.2, 147.4, 136.9, 133.7, 133.0, 132.5, 129.7, 128.9, 126.4, 124.0, 122.3, 113.4, 78.9, 73.0, 46.4, 44.5, 40.9, 40.6, 36.3, 35.0, 33.2, 29.1, 27.2, 25.1, 23.6, 23.1, 16.8, 14.1, 13.8, 12.9, 9.53, 8.41; HR-MS (ESI): calcd for C$_{42}$H$_{71}$NO$_4$SnI$^+$ [M+H$^+$]: 900.3444. found: 900.3442.

o. Preparation of Compound 26

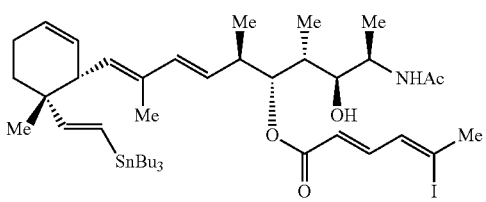

To a stirred solution of ester 25 (17 mg, 18.9 µmol) in CH$_2$Cl$_2$ (1 mL) was added a solution of Ti(O-i-Pr)$_4$ (49 µL, 0.77M in CH$_2$Cl$_2$, 37.9 µmol) in CH$_2$Cl$_2$ at room temperature. Stirred at room temperature for 8 hrs, the reaction was quenched with saturated aqueous NaHCO$_3$ (2 mL) and diluted with CH$_2$Cl$_2$ (10 mL). The organic phase was separated, and the aqueous phase was extracted with CH$_2$Cl$_2$ (5 mL×3). The combined organic layers were washed with brine, dried over Na$_2$SO$_4$, concentrated, and purified by flash chromatography (hexanes/EtOAc=1:1-1:2) to give ester 26 (14 mg) as colorless oil in 82% yield. Data for compound 26: [α]$_D{}^{23}$=+42.4 (c=1.00 in CHCl$_3$); $^1$H NMR (300 MHz, CDCl$_3$) δ 7.32 (1H, dd, J=10.5, 15.3 Hz), 6.21 (2H, d, J=9.3 Hz), 6.11 (1H, d, J=19.5 Hz), 6.03 (1H, d, J=15.6 Hz), 5.93 (1H, d, J=15.0 Hz), 5.84 (1H, d, J=19.5 Hz), 5.67 dd, J=2.4, 9.6 Hz), 5.38-5.30 (2H, m), 5.22 (1H, d, J=10.2 Hz), 4.98 (1H, d, J=9.3 Hz), 4.19-4.15 (1H, m), 3.99 (1H, d, J=3.9 Hz), 3.10 (1H, ddd, J=3.0, 3.9, 10.2 Hz), 2.89-2.84 (1H, m), 2.68 (3H, s), 2.55 (1H, dd, J=7.8, 15.9 Hz), 2.07-2.01 (2H, m), 1.95 (3H, s), 1.84-1.74 (1H, m), 1.64 (3H, s), 1.57-1.43 (8H, m), 1.37-1.23 (6H, m), 1.06 (3H, d, J=6.6 Hz), 1.01 (3H, d, J=6.9 Hz), 0.93-0.82 (21H, m); $^{13}$C NMR (75 MHz, CDCl$_3$) 169.0, 168.3, 154.2, 147.5, 136.1, 133.4, 133.0, 132.5, 129.0, 128.6, 126.4, 123.9, 122.1, 113.2, 77.9, 73.2, 45.3, 44.5, 40.6, 38.7, 37.5, 34.9, 33.9, 29.2, 27.3, 25.1, 23.6, 23.2, 17.1, 13.8, 12.9, 12.7, 9.55, 8.50; HR-MS (ESI): calcd for C$_{42}$H$_{71}$NO$_4$SnI$^+$ [M+H$^+$]: 900.3444. found: 900.3471.

Example 2

Compound 3 was tested in the NCI-60 cell assay and was found to be active against leukemia, non-small cell lung cancer, colon cancer, CNS cancer, melanoma, ovarian cancer, renal cancer, prostate cancer, and breast cancer.

Example 3

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |

| (vi) Aerosol | mg/can |
|---|---|
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of formula I:

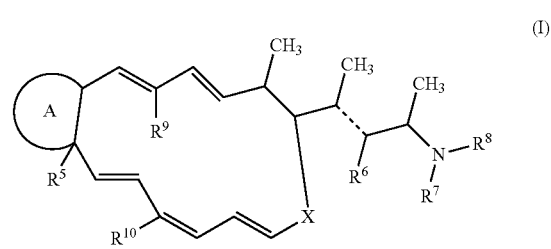

wherein:
Ring A is a 5-7 membered monocyclic or an 8-12 membered bicyclic, saturated, partially unsaturated, or aromatic, carbocyclic or heterocyclic ring system that is optionally substituted with one or more groups independently selected from hydroxy, halo, nitro, cyano, trifluoromethoxy, $(C_1-C_6)$alkyl, $(C_1-C_6)$alkoxy, $(C_1-C_6)$alkanoyl, $(C_1-C_6)$alkoxycarbonyl, or $(C_3-C_6)$cycloalkyl, wherein the $(C_3-C_6)$cycloalkyl and $(C_1-C_6)$alkyl are each optionally substituted with one or more OH, SH, halo, or $N(R_a)_2$;

$R^5$ is H, hydroxy, mercapto (—SH), halo, $N(R_a)_2$, or $(C_1-C_6)$alkyl, wherein the $(C_1-C_6)$alkyl is optionally substituted with one or more hydroxy, mercapto, halo, or $N(R_a)_2$; or $R^5$ is absent when it is not required to fill the valence requirements of the ring A atom to which it is attached;

either the bond represented by ---- is a double bond and $R^6$ is H; or the bond represented by ---- is a single bond and $R^6$ is hydroxy, H or $N(R_b)_2$;

$R^7$ is H, $(C_3-C_6)$cycloalkyl, or $(C_1-C_6)$alkyl;

$R^8$ is —C(=O)$R_c$, —C(=O)O$R_c$, —S(=O)$R_c$, —S(=O)$_2R_c$, —C(=O)N$R_dR_e$;

$R^9$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;

$R^{10}$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;

X is —C(=O)—O—, —O—C(=O)—, —C(=O)—NR$_a$—, —NR$_a$C(=O)—, —O—C(=O)—NR$_a$—, —NR$_a$—C(=O)—O—, —O—C(=O)—O—, or —NR$_a$—C(=O)—NR$_a$—;

each $R_a$ is independently H or $(C_1-C_6)$alkyl;
each $R_b$ is independently H or $(C_1-C_6)$alkyl;

$R_c$ is H, $(C_3$-$C_6)$cycloalkyl, or $(C_1$-$C_6)$alkyl;
$R_d$ is H, $(C_3$-$C_6)$cycloalkyl, or $(C_1$-$C_6)$alkyl; and
$R_e$ is H, $(C_3$-$C_6)$cycloalkyl, or $(C_1$-$C_6)$alkyl;
or a salt thereof.

2. The compound of claim 1 which is a compound of formula Ia:

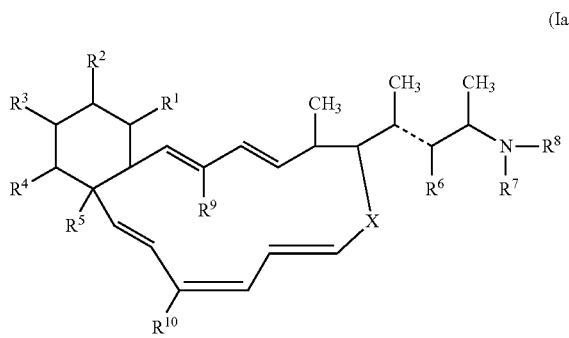

(Ia)

wherein:
- $R^1$ and $R^2$ are each independently H, halo, $(C_3$-$C_6)$cycloalkyl, or $(C_1$-$C_6)$alkyl, wherein the $(C_3$-$C_6)$cycloalkyl and $(C_1$-$C_6)$alkyl are each optionally substituted with one or more OH, SH, halo, or $N(R_a)_2$; or $R^1$ and $R^2$ taken together with the atoms to which they are attached form a double bond;
- $R^3$ is H, halo, $(C_3$-$C_6)$cycloalkyl, or $(C_1$-$C_6)$alkyl, wherein the $(C_3$-$C_6)$cycloalkyl and $(C_1$-$C_6)$alkyl are each optionally substituted with one or more OH, SH, halo, or $N(R_a)_2$; and $R^4$ is H, halo, $(C_3$-$C_6)$cycloalkyl, or $(C_1$-$C_6)$alkyl, wherein the $(C_3$-$C_6)$cycloalkyl and $(C_1$-$C_6)$alkyl are each optionally substituted with one or more OH, SH, halo, or $N(R_a)_2$; or $R^3$ and $R^4$ taken together with the atoms to which they are attached form a 5, 6, or 7 membered saturated, partially unsaturated, or aromatic carbocyclic or heterocyclic ring, which ring is optionally substituted with one or more groups independently selected from hydroxy, halo, nitro, cyano, trifluoromethyl, $CF_3$, $CH_2F$, $CHF_2$, F, trifluoromethoxy, $(C_1$-$C_6)$alkyl, $(C_1$-$C_6)$alkoxy, $(C_1$-$C_6)$alkanoyl, or $(C_1$-$C_6)$alkoxycarbonyl;
- $R^5$ is H, hydroxy, mercapto (—SH), halo, $N(R_a)_2$, or $(C_1$-$C_6)$alkyl, wherein the $(C_1$-$C_6)$alkyl is optionally substituted with one or more hydroxy, mercapto, halo, or $N(R_a)_2$;
- either the bond represented by ---- is a double bond and $R^6$ is H; or the bond represented by ---- is a single bond and $R^6$ is H, hydroxy, or $N(R_b)_2$;
- $R^7$ is H, $(C_3$-$C_6)$cycloalkyl, or $(C_1$-$C_6)$alkyl;
- $R^8$ is —C(=O)$R_c$, —C(=O)O$R_c$, —S(=O)$R_c$, —S(=O)$_2R_c$, —C(=O)N$R_dR_e$;
- $R^9$ is H, halo, $(C_3$-$C_6)$cycloalkyl, or $(C_1$-$C_6)$alkyl, wherein the $(C_3$-$C_6)$cycloalkyl and $(C_1$-$C_6)$alkyl are each optionally substituted with one or more OH, SH, halo, or $N(R_a)_2$;
- $R^{10}$ is H, halo, $(C_3$-$C_6)$cycloalkyl, or $(C_1$-$C_6)$alkyl, wherein the $(C_3$-$C_6)$cycloalkyl and $(C_1$-$C_6)$alkyl are each optionally substituted with one or more OH, SH, halo, or $N(R_a)_2$;
- X is —C(=O)—O—, —O—C(=O)—, —C(=O)—$NR_a$—, —$NR_a$C(=O)—, —O—C(=O)—$NR_a$—, —$NR_a$—C(=O)—O—, —O—C(=O)—O—, or —$NR_a$—C(=O)—$NR_a$—;
- each $R_a$ is independently H or $(C_1$-$C_6)$alkyl;

each $R_b$ is independently H or $(C_1$-$C_6)$alkyl;
$R_c$ is H, $(C_3$-$C_6)$cycloalkyl, or $(C_1$-$C_6)$alkyl;
$R_d$ is H, $(C_3$-$C_6)$cycloalkyl, or $(C_1$-$C_6)$alkyl; and
$R_e$ is H, $(C_3$-$C_6)$cycloalkyl, or $(C_1$-$C_6)$alkyl;
or a salt thereof.

3. The compound of claim 2 which is a compound of formula Ib:

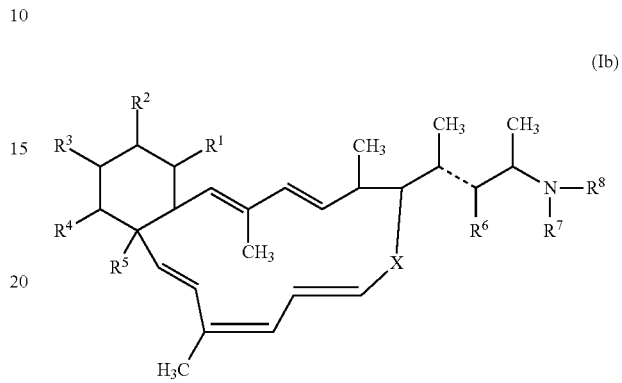

(Ib)

or a salt thereof.

4. The compound of claim 2 which is a compound of formula (Ic):

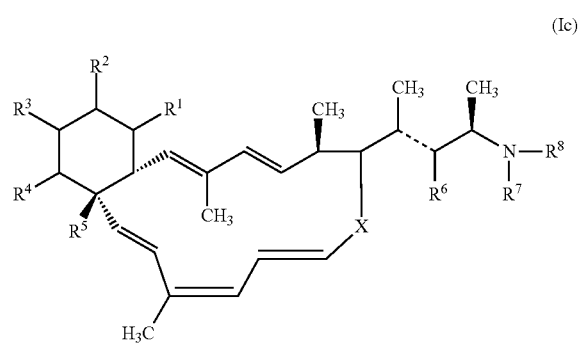

(Ic)

or a salt thereof.

5. The compound of claim 2 which is a compound of formula Id:

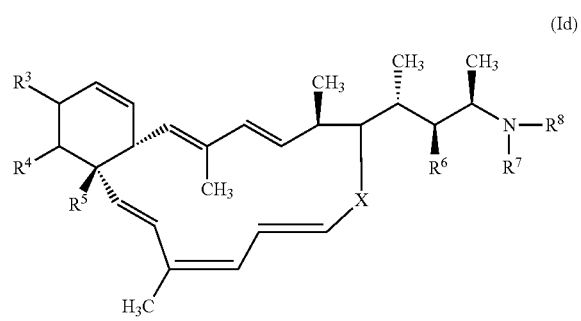

(Id)

or a salt thereof.

6. The compound of claim 1 which is a compound of formula Ia:

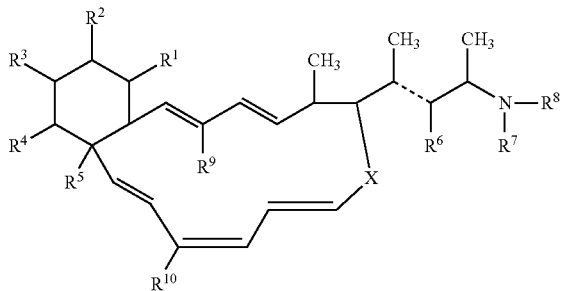

wherein:
- $R^1$ and $R^2$ are each independently H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$; or $R^1$ and $R^2$ taken together with the atoms to which they are attached form a double bond;
- $R^3$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$; and $R^4$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$; or $R^3$ and $R^4$ taken together with the atoms to which they are attached form a 5, 6, or 7 membered saturated, partially unsaturated, or aromatic carbocyclic or heterocyclic ring, which ring is optionally substituted with one or more groups independently selected from hydroxy, halo, nitro, cyano, trifluoromethyl, $CF_3$, $CH_2F$, $CHF_2$, F, trifluoromethoxy, $(C_1-C_6)$alkyl, $(C_1-C_6)$alkoxy, $(C_1-C_6)$alkanoyl, or $(C_1-C_6)$alkoxycarbonyl;
- $R^5$ is H, hydroxy, mercapto (—SH), halo, $N(R_a)_2$, or $(C_1-C_6)$alkyl, wherein the $(C_1-C_6)$alkyl is optionally substituted with one or more hydroxy, mercapto, halo, or $N(R_a)_2$;
- either the bond represented by ---- is a double bond and $R^6$ is H; or the bond represented by ---- is a single bond and $R^6$ is H, hydroxy, or $N(R_b)_2$;
- $R^7$ is H, $(C_3-C_6)$cycloalkyl, or $(C_1-C_6)$alkyl;
- $R^8$ is —C(=O)$R_c$, —C(=O)O$R_c$, —S(=O)$R_c$, —S(=O)$_2R_c$, —C(=O)N$R_dR_e$;
- $R^9$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;
- $R^{10}$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;
- X is —C(=O)—O—, —O—C(=O)—, —C(=O)—$NR_a$—, —$NR_a$C(=O)—, —O—C(=O)—$NR_a$—, —$NR_a$—C(=O)—O—, —O—C(=O)—O—, or —$NR_a$—C(=O)—$NR_a$—;
- each $R_a$ is independently H or $(C_1-C_6)$alkyl;
- each $R_b$ is independently H or $(C_1-C_6)$alkyl;
- $R_c$ is H, $(C_3-C_6)$cycloalkyl, or $(C_1-C_6)$alkyl;
- $R_d$ is H, $(C_3-C_6)$cycloalkyl, or $(C_1-C_6)$alkyl; and
- $R_e$ is H, $(C_3-C_6)$cycloalkyl, or $(C_1-C_6)$alkyl;
- or a salt thereof, wherein $R^1$ and $R^2$ are each H.

7. The compound of claim 2 wherein $R^1$ and $R^2$ taken together with the atoms to which they are attached form a double bond.

8. The compound of claim 2 wherein $R^3$ is H.

9. The compound of claim 2 wherein $R^4$ is H.

10. The compound of claim 1 wherein $R^5$ is methyl.

11. The compound of claim 1 which is a compound of formula Ia:

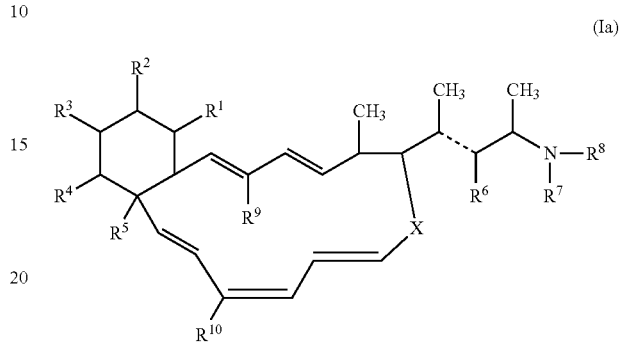

wherein:
- $R^1$ and $R^2$ are each independently H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$; or $R^1$ and $R^2$ taken together with the atoms to which they are attached form a double bond;
- $R^3$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$; and $R^4$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$; or $R^3$ and $R^4$ taken together with the atoms to which they are attached form a 5, 6, or 7 membered saturated, partially unsaturated, or aromatic carbocyclic or heterocyclic ring, which ring is optionally substituted with one or more groups independently selected from hydroxy, halo, nitro, cyano, trifluoromethyl, $CF_3$, $CH_2F$, $CHF_2$, F, trifluoromethoxy, $(C_1-C_6)$alkyl, $(C_1-C_6)$alkoxy, $(C_1-C_6)$alkanoyl, or $(C_1-C_6)$alkoxycarbonyl;
- $R^5$ is H, hydroxy, mercapto (—SH), halo, $N(R_a)_2$, or $(C_1-C_6)$alkyl, wherein the $(C_1-C_6)$alkyl is optionally substituted with one or more hydroxy, mercapto, halo, or $N(R_a)_2$;
- either the bond represented by ---- is a double bond and $R^6$ is H; or the bond represented by ---- is a single bond and $R^6$ is H, hydroxy, or $N(R_b)_2$;
- $R^7$ is H, $(C_3-C_6)$cycloalkyl, or $(C_1-C_6)$alkyl;
- $R^8$ is —C(=O)$R_c$, —C(=O)O$R_c$, —S(=O)$R_c$, —S(=O)$_2R_c$, —C(=O)N$R_dR_e$;
- $R^9$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;
- $R^{10}$ is H, halo, $(C_3-C_6)$cycloalkyl, or $(C_1-C_6)$alkyl, wherein the $(C_3-C_6)$cycloalkyl and $(C_1-C_6)$alkyl are each optionally substituted with one or more OH, SH, halo, or $N(R_a)_2$;
- X is —C(=O)—O—, —O—C(=O)—, —C(=O)—$NR_a$—, —$NR_a$C(=O)—, —O—C(=O)—$NR_a$—, —$NR_a$C(=O)—O—, —O—C(=O)—O—, or —$NR_a$—C(=O)—$NR_a$—;

each $R_a$ is independently H or $(C_1\text{-}C_6)$alkyl;
each $R_b$ is independently H or $(C_1\text{—}C)$alkyl;
$R_c$ is H, $(C_3\text{-}C_6)$cycloalkyl, or $(C_1\text{-}C_6)$alkyl;
$R_d$ is H, $(C_3\text{-}C_6)$cycloalkyl, or $(C_1\text{-}C_6)$alkyl; and
$R_e$ is H, $(C_3\text{-}C_6)$cycloalkyl, or $(C_1\text{-}C_6)$alkyl;
or a salt thereof, wherein the bond represented by ---- is a double bond and $R^6$ is H.

12. The compound of claim 1 wherein the bond represented by ---- is a single bond and $R^6$ is hydroxy.

13. The compound of claim 1 wherein $R^7$ is H.

14. The compound of claim 1 wherein $R^8$ is —C(=O)$R_c$.

15. The compound of claim 1 wherein X is —C(=O)—O— or —O—C(=O)—.

16. The compound of claim 1 wherein X is —C(=O)—$NR_a$— or —$NR_a$C(=O)—.

17. The compound of claim 1 wherein X is —C(=O)—O—.

18. A pharmaceutical composition comprising a compound as described in claim 1 or a pharmaceutically acceptable salt thereof and a pharmaceutically acceptable diluent or carrier.

19. A method for treating or preventing cancer in an animal comprising administering a compound as described in claim 1 or a pharmaceutically acceptable salt thereof to the animal.

* * * * *